(12) United States Patent
Yun et al.

(10) Patent No.: US 10,416,099 B2
(45) Date of Patent: Sep. 17, 2019

(54) METHOD OF PERFORMING X-RAY SPECTROSCOPY AND X-RAY ABSORPTION SPECTROMETER SYSTEM

(71) Applicant: Sigray, Inc., Concord, CA (US)

(72) Inventors: Wenbing Yun, Walnut Creek, CA (US); Srivatsan Seshadri, Pleasnton, CA (US); Sylvia Jia Yun Lewis, San Francisco, CA (US); Janos Kirz, Berkeley, CA (US); Alan Francis Lyon, Berkeley, CA (US); Benjamin Donald Stripe, Walnut Creek, CA (US)

(73) Assignee: Sigray, Inc., Concord, CA (US)

( * ) Notice: Subject to any disclaimer, the term of this patent is extended or adjusted under 35 U.S.C. 154(b) by 0 days.

(21) Appl. No.: 15/927,520

(22) Filed: Mar. 21, 2018

(65) Prior Publication Data

US 2019/0011379 A1    Jan. 10, 2019

Related U.S. Application Data

(63) Continuation-in-part of application No. 15/431,786, filed on Feb. 14, 2017, which is a continuation-in-part
(Continued)

(51) Int. Cl.
*G01N 23/00* (2006.01)
*G01N 23/085* (2018.01)
(Continued)

(52) U.S. Cl.
CPC ............. *G01N 23/085* (2018.02); *G21K 1/06* (2013.01); *H01J 35/02* (2013.01); *H01J 35/10* (2013.01); *H01J 35/12* (2013.01)

(58) Field of Classification Search
CPC ......................... G01N 23/085; G01N 23/083
See application file for complete search history.

(56) References Cited

U.S. PATENT DOCUMENTS 1,203,495 A   10/1916  Coolidge
1,211,092 A    1/1917  Coolidge
(Continued)

FOREIGN PATENT DOCUMENTS

CN   102124537 A   7/2011
CN   102551761 A   7/2012
(Continued)

OTHER PUBLICATIONS

"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.
(Continued)

*Primary Examiner* — Dani Fox
(74) *Attorney, Agent, or Firm* — Knobbe, Martens, Olson & Bear, LLP

(57) ABSTRACT

A method for performing x-ray absorption spectroscopy and an x-ray absorption spectrometer system to be used with a compact laboratory x-ray source to measure x-ray absorption of the element of interest in an object with both high spatial and high spectral resolution. The spectrometer system comprises a compact high brightness laboratory x-ray source, an optical train to focus the x-rays through an object to be examined, and a spectrometer comprising a single crystal analyzer (and, in some embodiments, also a mosaic crystal) to disperse the transmitted beam onto a spatially resolving x-ray detector. The high brightness/high flux x-ray source may have a take-off angle between 0 and 105 mrad. and be coupled to an optical train that collects and focuses the high flux x-rays to spots less than 500 micrometers, leading to high flux density. The coatings of the optical train may also act as a "low-pass" filter, allowing a predetermined
(Continued)

bandwidth of x-rays to be observed at one time while excluding the higher harmonics.

20 Claims, 19 Drawing Sheets

Related U.S. Application Data of application No. 15/269,855, filed on Sep. 19, 2016, now Pat. No. 9,570,265, which is a continuation-in-part of application No. 14/636,994, filed on Mar. 3, 2015, now Pat. No. 9,448,190, and a continuation-in-part of application No. 14/544,191, filed on Dec. 5, 2014, now Pat. No. 9,449,781, said application No. 15/431,786 is a continuation-in-part of application No. 15/166,274, filed on May 27, 2016, which is a continuation-in-part of application No. 14/999,147, filed on Apr. 1, 2016, now Pat. No. 9,543,109, which is a continuation of application No. 14/490,672, filed on Sep. 19, 2014, now Pat. No. 9,390,881.

(60) Provisional application No. 62/475,213, filed on Mar. 22, 2017, provisional application No. 62/008,856, filed on Jun. 6, 2014, provisional application No. 62/086,132, filed on Dec. 1, 2014, provisional application No. 62/117,062, filed on Feb. 17, 2015, provisional application No. 61/912,478, filed on Dec. 5, 2013, provisional application No. 61/912,486, filed on Dec. 5, 2013, provisional application No. 61/946,475, filed on Feb. 28, 2014, provisional application No. 62/155,449, filed on Apr. 30, 2015, provisional application No. 62/141,847, filed on Apr. 1, 2015, provisional application No. 61/931,519, filed on Jan. 24, 2014, provisional application No. 61/894,073, filed on Oct. 22, 2013, provisional application No. 61/880,151, filed on Sep. 19, 2013.

(51) Int. Cl.
*G21K 1/06* (2006.01)
*H01J 35/02* (2006.01)
*H01J 35/10* (2006.01)
*H01J 35/12* (2006.01)

(56) References Cited

U.S. PATENT DOCUMENTS

| | | |
|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,165,472 A | 8/1979 | Wittry |
| 4,266,138 A | 5/1981 | Nelson et al. |
| 4,277,112 A | 7/1981 | Heshmat |
| 4,426,718 A | 1/1984 | Hayashi et al. |
| 4,523,327 A | 6/1985 | Eversole |
| 4,573,186 A | 2/1986 | Reinhold |
| 4,807,268 A | 2/1989 | Wittrey |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,132,997 A | 7/1992 | Kojima |
| 5,148,462 A | 9/1992 | Spitsyn et al. |
| 5,173,928 A | 12/1992 | Momose et al. |
| 5,249,216 A | 9/1993 | Ohsugi et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,715,291 A | 2/1998 | Momose |
| 5,729,583 A | 3/1998 | Tang et al. |
| 5,737,387 A | 4/1998 | Smither |
| 5,768,339 A | 6/1998 | O'Hara |
| 5,772,903 A | 6/1998 | Hirsch |
| 5,778,039 A | 7/1998 | Hossain |
| 5,812,629 A | 9/1998 | Clauser |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 5,881,126 A | 3/1999 | Momose |
| 5,912,940 A | 6/1999 | O'Hara |
| 5,930,325 A | 7/1999 | Momose |
| 6,108,397 A | 8/2000 | Cash, Jr. |
| 6,108,398 A | 8/2000 | Mazor et al. |
| 6,125,167 A | 9/2000 | Morgan |
| 6,278,764 B1 | 8/2001 | Barbee, Jr. et al. |
| 6,307,916 B1 | 10/2001 | Rogers et al. |
| 6,359,964 B1 | 3/2002 | Kogan |
| 6,377,660 B1 | 4/2002 | Ukita et al. |
| 6,381,303 B1 | 4/2002 | Vu et al. |
| 6,389,100 B1 | 5/2002 | Verman et al. |
| 6,430,254 B2 | 8/2002 | Wilkins |
| 6,442,231 B1 | 8/2002 | O'Hara |
| 6,456,688 B1 | 9/2002 | Taguchi et al. |
| 6,463,123 B1 | 10/2002 | Korenev |
| 6,487,272 B1 | 11/2002 | Kutsuzawa |
| 6,504,902 B2 | 1/2003 | Iwasaki et al. |
| 6,507,388 B2 | 1/2003 | Burghoorn |
| 6,553,096 B1 | 4/2003 | Zhou et al. |
| 6,560,313 B1 | 5/2003 | Harding et al. |
| 6,560,315 B1 | 5/2003 | Price et al. |
| 6,707,883 B1 | 3/2004 | Tiearney et al. |
| 6,711,234 B1 | 3/2004 | Loxley et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,870,172 B1 | 3/2005 | Mankos et al. |
| 6,885,503 B2 | 4/2005 | Yun et al. |
| 6,914,723 B2 | 7/2005 | Yun et al. |
| 6,917,472 B1 | 7/2005 | Yun et al. |
| 6,947,522 B2 | 9/2005 | Wilson et al. |
| 6,975,703 B2 | 12/2005 | Wilson et al. |
| 7,003,077 B2 | 2/2006 | Jen et al. |
| 7,006,596 B1 | 2/2006 | Janik |
| 7,015,467 B2 | 3/2006 | Maldonado et al. |
| 7,023,955 B2 | 4/2006 | Chen et al. |
| 7,057,187 B1 | 6/2006 | Yun et al. |
| 7,079,625 B2 | 7/2006 | Lenz |
| 7,095,822 B1 | 8/2006 | Yun |
| 7,110,503 B1 | 9/2006 | Kumakhov |
| 7,119,953 B2 | 10/2006 | Yun et al. |
| 7,130,375 B1 | 10/2006 | Yun et al. |
| 7,170,969 B1 | 1/2007 | Yun et al. |
| 7,180,979 B2 | 2/2007 | Momose |
| 7,180,981 B2 | 2/2007 | Wang |
| 7,183,547 B2 | 2/2007 | Yun et al. |
| 7,215,736 B1 | 5/2007 | Wang et al. |
| 7,215,741 B2 | 5/2007 | Ukita et al. |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,268,945 B2 | 9/2007 | Yun et al. |
| 7,286,640 B2 | 10/2007 | Yun et al. |
| 7,297,959 B2 | 11/2007 | Yun et al. |
| 7,298,826 B2 | 11/2007 | Inazuru |
| 7,330,533 B2 | 2/2008 | Sampayon |
| 7,346,148 B2 | 3/2008 | Ukita |

(56) References Cited

U.S. PATENT DOCUMENTS

| | | |
|---|---|---|
| 7,346,204 B2 | 3/2008 | Ito |
| 7,349,525 B2 | 3/2008 | Morton |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert et al. |
| 7,388,942 B2 | 6/2008 | Wang et al. |
| 7,394,890 B1 | 7/2008 | Wang et al. |
| 7,400,704 B1 | 7/2008 | Yun et al. |
| 7,406,151 B1 | 7/2008 | Yun |
| 7,412,024 B1 | 8/2008 | Yun et al. |
| 7,412,030 B1 | 8/2008 | O'Hara |
| 7,412,131 B2 | 8/2008 | Lee et al. |
| 7,414,787 B2 | 8/2008 | Yun et al. |
| 7,433,444 B2 | 10/2008 | Baumann |
| 7,440,542 B2 | 10/2008 | Baumann |
| 7,443,953 B1 | 10/2008 | Yun et al. |
| 7,453,981 B2 | 11/2008 | Baumann |
| 7,463,712 B2 | 12/2008 | Zhu et al. |
| 7,486,770 B2 | 2/2009 | Baumann |
| 7,492,871 B2 | 2/2009 | Popescu |
| 7,499,521 B2 | 3/2009 | Wang et al. |
| 7,515,684 B2 | 4/2009 | Gibson et al. |
| 7,522,698 B2 | 4/2009 | Popescu |
| 7,522,707 B2 | 4/2009 | Steinlage et al. |
| 7,522,708 B2 | 4/2009 | Heismann |
| 7,529,343 B2 | 5/2009 | Safai et al. |
| 7,532,704 B2 | 5/2009 | Hempel |
| 7,551,719 B2 | 6/2009 | Yokhin et al. |
| 7,551,722 B2 | 6/2009 | Ohshima et al. |
| 7,561,662 B2 | 7/2009 | Wang et al. |
| 7,564,941 B2 | 7/2009 | Baumann |
| 7,583,789 B1 | 9/2009 | Macdonald et al. |
| 7,601,399 B2 | 10/2009 | Barnola et al. |
| 7,639,786 B2 | 12/2009 | Baumann |
| 7,646,843 B2 | 1/2010 | Popescu et al. |
| 7,672,433 B2 | 3/2010 | Zhong et al. |
| 7,680,243 B2 | 3/2010 | Yokhin et al. |
| 7,787,588 B1 | 8/2010 | Yun et al. |
| 7,796,725 B1 | 9/2010 | Yun et al. |
| 7,796,726 B1 | 9/2010 | Gendreau et al. |
| 7,800,072 B2 | 9/2010 | Yun et al. |
| 7,809,113 B2 | 10/2010 | Aoki et al. |
| 7,813,475 B1 | 10/2010 | Wu et al. |
| 7,817,777 B2 | 10/2010 | Baumann et al. |
| 7,864,426 B2 | 1/2011 | Yun et al. |
| 7,864,922 B2 | 1/2011 | Kawabe |
| 7,873,146 B2 | 1/2011 | Okunuki et al. |
| 7,876,883 B2 | 1/2011 | O'Hara |
| 7,889,838 B2 | 2/2011 | David et al. |
| 7,889,844 B2 | 2/2011 | Okunuki et al. |
| 7,914,693 B2 | 3/2011 | Jeong et al. |
| 7,920,673 B2 | 4/2011 | Lanza et al. |
| 7,920,676 B2 | 4/2011 | Yun et al. |
| 7,924,973 B2 | 4/2011 | Kottler et al. |
| 7,929,667 B1 | 4/2011 | Zhuang et al. |
| 7,945,018 B2 | 5/2011 | Heismann |
| 7,949,092 B2 | 5/2011 | Brons et al. |
| 7,949,095 B2 | 5/2011 | Ning |
| 7,974,379 B1 | 7/2011 | Case et al. |
| 7,983,381 B2 | 7/2011 | David et al. |
| 7,991,120 B2 | 8/2011 | Okunuki et al. |
| 8,005,185 B2 | 8/2011 | Popescu |
| 8,009,796 B2 | 8/2011 | Popescu |
| 8,009,797 B2 | 8/2011 | Ouchi |
| 8,041,004 B2 | 10/2011 | David |
| 8,036,341 B2 | 11/2011 | Lee |
| 8,058,621 B2 | 11/2011 | Kommareddy et al. |
| 8,068,579 B1 | 11/2011 | Yun et al. |
| 8,073,099 B2 | 12/2011 | Niu et al. |
| 8,094,784 B2 | 1/2012 | Morton |
| 8,139,711 B2 | 3/2012 | Takahashi |
| 8,139,716 B2 | 3/2012 | Okunuki et al. |
| 8,184,771 B2 | 5/2012 | Murakoshi |
| 8,208,602 B2 | 6/2012 | Lee et al. |
| 8,208,603 B2 | 6/2012 | Sato |
| 8,233,587 B2 | 7/2012 | Sato |
| 8,243,879 B2 | 8/2012 | Itoh et al. |
| 8,243,884 B2 | 8/2012 | Rödhammer et al. |
| 8,280,000 B2 | 10/2012 | Takahashi |
| 8,306,183 B2 | 11/2012 | Koehler |
| 8,306,184 B2 | 11/2012 | Chang et al. |
| 8,351,569 B2 | 1/2013 | Baker |
| 8,351,570 B2 | 1/2013 | Nakamura |
| 8,353,628 B1 | 1/2013 | Yun et al. |
| 8,360,640 B2 | 1/2013 | Reinhold |
| 8,374,309 B2 | 2/2013 | Donath |
| 8,406,378 B2 | 3/2013 | Wang et al. |
| 8,416,920 B2 | 4/2013 | Okumura et al. |
| 8,422,633 B2 | 4/2013 | Lantz et al. |
| 8,451,975 B2 | 5/2013 | Tada |
| 8,422,637 B2 | 6/2013 | Okunuki et al. |
| 8,509,386 B2 | 8/2013 | Lee et al. |
| 8,520,803 B2 | 8/2013 | Behling |
| 8,526,575 B1 | 9/2013 | Yun et al. |
| 8,532,257 B2 | 9/2013 | Mukaide et al. |
| 8,553,843 B2 | 10/2013 | Drory |
| 8,559,594 B2 | 10/2013 | Ouchi |
| 8,559,597 B2 | 10/2013 | Chen et al. |
| 8,565,371 B2 | 10/2013 | Bredno |
| 8,576,983 B2 | 11/2013 | Baeumer |
| 8,591,108 B2 | 11/2013 | Tada |
| 8,602,648 B1 | 12/2013 | Jacobsen et al. |
| 8,632,247 B2 | 1/2014 | Ishii |
| 8,666,024 B2 | 3/2014 | Okunuki et al. |
| 8,666,025 B2 | 3/2014 | Klausz |
| 8,699,667 B2 | 4/2014 | Steinlage et al. |
| 8,735,844 B1 | 5/2014 | Khaykovich et al. |
| 8,737,565 B1 | 5/2014 | Lyon et al. |
| 8,744,048 B2 | 6/2014 | Lee et al. |
| 8,755,487 B2 | 6/2014 | Kaneko |
| 8,767,915 B2 | 7/2014 | Stutman |
| 8,767,916 B2 | 7/2014 | Hashimoto |
| 8,781,069 B2 | 7/2014 | Murakoshi |
| 8,824,629 B2 | 9/2014 | Ishii |
| 8,831,174 B2 | 9/2014 | Kohara |
| 8,831,175 B2 | 9/2014 | Silver et al. |
| 8,831,179 B2 | 9/2014 | Adler et al. |
| 8,855,265 B2 | 10/2014 | Engel |
| 8,861,682 B2 | 10/2014 | Okunuki et al. |
| 8,903,042 B2 | 12/2014 | Ishii |
| 8,908,824 B2 | 12/2014 | Kondoh |
| 8,995,622 B2 | 3/2015 | Adler et al. |
| 9,001,967 B2 | 4/2015 | Baturin |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,063,055 B2 | 6/2015 | Ouchi |
| 9,129,715 B2 | 9/2015 | Adler et al. |
| 9,222,899 B2 | 12/2015 | Yamaguchi |
| 9,257,254 B2 | 2/2016 | Ogura et al. |
| 9,263,225 B2 | 2/2016 | Morton |
| 9,329,141 B2 | 5/2016 | Stutman |
| 9,357,975 B2 | 6/2016 | Baturin |
| 9,390,881 B2 | 7/2016 | Yun et al. |
| 9,439,613 B2 | 9/2016 | Stutman |
| 9,448,190 B2 | 9/2016 | Yun et al. |
| 9,449,781 B2 | 9/2016 | Yun et al. |
| 9,494,534 B2 | 11/2016 | Baturin |
| 9,543,109 B2 | 1/2017 | Yun et al. |
| 9,564,284 B2 | 2/2017 | Gerzoskovitz |
| 9,570,265 B1 | 2/2017 | Yun et al. |
| 9,594,036 B2 | 3/2017 | Yun et al. |
| 9,632,040 B2 | 4/2017 | Stutman |
| 9,719,947 B2 | 8/2017 | Yun et al. |
| 9,757,081 B2 | 9/2017 | Proksa |
| 9,761,021 B2 | 9/2017 | Koehler |
| 9,823,203 B2 | 11/2017 | Yun et al. |
| 9,826,949 B2 | 11/2017 | Ning |
| 9,837,178 B2 | 12/2017 | Nagai |
| 9,842,414 B2 | 12/2017 | Koehler |
| 9,861,330 B2 | 1/2018 | Rossl |
| 9,874,531 B2 | 1/2018 | Yun et al. |
| 9,881,710 B2 | 1/2018 | Roessl |

(56) References Cited

U.S. PATENT DOCUMENTS

| | | |
|---|---|---|
| 9,916,655 B2 | 3/2018 | Sampanoni |
| 9,939,392 B2 | 4/2018 | Wen |
| 9,970,119 B2 | 5/2018 | Yokoyama |
| 10,014,148 B2 | 7/2018 | Tang et al. |
| 10,028,716 B2 | 7/2018 | Rossl |
| 10,045,753 B2 | 8/2018 | Teshima |
| 10,068,740 B2 | 9/2018 | Gupta |
| 10,074,451 B2 | 9/2018 | Kottler et al. |
| 10,085,701 B2 | 10/2018 | Hoshino |
| 10,141,081 B2 | 11/2018 | Preusche |
| 10,151,713 B2 | 12/2018 | Wu et al. |
| 10,153,062 B2 | 12/2018 | Gall et al. |
| 10,176,297 B2 | 1/2019 | Zerhusen et al. |
| 10,182,194 B2 | 1/2019 | Karim et al. |
| 2001/0006413 A1 | 7/2001 | Burghoorn |
| 2002/0085676 A1 | 7/2002 | Snyder |
| 2003/0142790 A1 | 1/2003 | Zhou et al. |
| 2003/0223536 A1 | 12/2003 | Yun et al. |
| 2004/0047446 A1 | 3/2004 | Platonov |
| 2004/0120463 A1 | 6/2004 | Wilson et al. |
| 2004/0140432 A1 | 7/2004 | Maldonado et al. |
| 2005/0074094 A1 | 4/2005 | Jen et al. |
| 2005/0123097 A1 | 6/2005 | Wang |
| 2005/0163284 A1 | 7/2005 | Inazuru |
| 2005/0282300 A1 | 12/2005 | Yun et al. |
| 2006/0045234 A1 | 3/2006 | Pelc et al. |
| 2006/0062350 A1 | 3/2006 | Yokhin |
| 2007/0030959 A1 | 2/2007 | Ritter |
| 2007/0071174 A1 | 3/2007 | Hebert et al. |
| 2007/0108387 A1 | 5/2007 | Yun et al. |
| 2007/0110217 A1 | 5/2007 | Ukita |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2008/0084966 A1 | 4/2008 | Aoki et al. |
| 2008/0089484 A1 | 4/2008 | Reinhold |
| 2008/0094694 A1 | 4/2008 | Yun et al. |
| 2008/0116398 A1 | 5/2008 | Hara |
| 2008/0159707 A1 | 7/2008 | Lee et al. |
| 2008/0165355 A1 | 7/2008 | Yasui et al. |
| 2008/0170662 A1 | 7/2008 | Reinhold |
| 2008/0170668 A1 | 7/2008 | Kruit et al. |
| 2008/0181363 A1 | 7/2008 | Fenter et al. |
| 2008/0240344 A1 | 10/2008 | Reinhold |
| 2008/0273662 A1 | 11/2008 | Yun |
| 2009/0052619 A1 | 2/2009 | Endoh |
| 2009/0092227 A1 | 4/2009 | David |
| 2009/0154640 A1 | 6/2009 | Baumann et al. |
| 2009/0316860 A1 | 12/2009 | Okunuki et al. |
| 2010/0012845 A1 | 1/2010 | Baeumer et al. |
| 2010/0027739 A1 | 2/2010 | Lantz et al. |
| 2010/0040202 A1 | 2/2010 | Lee |
| 2010/0046702 A1 | 2/2010 | Chen et al. |
| 2010/0061508 A1 | 3/2010 | Takahashi |
| 2010/0091947 A1 | 4/2010 | Niu |
| 2010/0141151 A1 | 6/2010 | Reinhold |
| 2010/0246765 A1 | 9/2010 | Murakoshi |
| 2010/0260315 A1 | 10/2010 | Sato et al. |
| 2010/0272239 A1 | 10/2010 | Lantz et al. |
| 2010/0284513 A1 | 11/2010 | Kawabe |
| 2011/0026680 A1 | 2/2011 | Sato |
| 2011/0038455 A1 | 2/2011 | Silver et al. |
| 2011/0058655 A1 | 3/2011 | Okumura et al. |
| 2011/0064191 A1* | 3/2011 | Toth ............... G01N 23/20033 378/53 |
| 2011/0085644 A1 | 4/2011 | Verman |
| 2011/0135066 A1 | 6/2011 | Behling |
| 2011/0142204 A1 | 6/2011 | Zou et al. |
| 2011/0235781 A1 | 9/2011 | Aoki et al. |
| 2011/0243302 A1 | 10/2011 | Murakoshi |
| 2011/0268252 A1* | 11/2011 | Ozawa ..................... G21K 1/06 378/82 |
| 2012/0041679 A1 | 2/2012 | Stampanoni |
| 2012/0057669 A1 | 3/2012 | Vogtmeier et al. |
| 2012/0163547 A1 | 6/2012 | Lee et al. |
| 2012/0163554 A1 | 6/2012 | Tada |
| 2012/0224670 A1 | 9/2012 | Kiyohara et al. |
| 2012/0228475 A1 | 9/2012 | Pang et al. |
| 2012/0269323 A1 | 10/2012 | Adler et al. |
| 2012/0269324 A1 | 10/2012 | Adler |
| 2012/0269325 A1 | 10/2012 | Adler et al. |
| 2012/0269326 A1 | 10/2012 | Adler et al. |
| 2012/0294420 A1 | 11/2012 | Nagai |
| 2013/0011040 A1 | 1/2013 | Kido et al. |
| 2013/0032727 A1 | 2/2013 | Kondoe |
| 2013/0039460 A1 | 2/2013 | Levy |
| 2013/0108012 A1 | 5/2013 | Sato |
| 2013/0108022 A1 | 5/2013 | Kugland et al. |
| 2013/0195246 A1 | 8/2013 | Tamura et al. |
| 2013/0223594 A1 | 8/2013 | Sprong et al. |
| 2013/0259207 A1 | 10/2013 | Omote et al. |
| 2013/0279651 A1 | 10/2013 | Yokoyama |
| 2013/0308112 A1 | 11/2013 | Clube et al. |
| 2013/0308754 A1 | 11/2013 | Yamazaki et al. |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0079188 A1 | 3/2014 | Hesselink et al. |
| 2014/0105363 A1 | 4/2014 | Chen et al. |
| 2014/0146945 A1 | 5/2014 | Fredenberg et al. |
| 2014/0153692 A1 | 6/2014 | Larkin et al. |
| 2014/0177800 A1 | 6/2014 | Sato et al. |
| 2014/0185778 A1 | 7/2014 | Lee et al. |
| 2014/0205057 A1 | 7/2014 | Koehler et al. |
| 2014/0211919 A1 | 7/2014 | Ogura et al. |
| 2014/0226785 A1 | 8/2014 | Stutman et al. |
| 2014/0241493 A1 | 8/2014 | Yokoyama |
| 2014/0270060 A1 | 9/2014 | Date et al. |
| 2014/0369469 A1 | 12/2014 | Ogura et al. |
| 2015/0030126 A1 | 1/2015 | Radicke |
| 2015/0030127 A1 | 1/2015 | Aoki et al. |
| 2015/0043713 A1 | 2/2015 | Chen |
| 2015/0049860 A1 | 2/2015 | Das |
| 2015/0055743 A1 | 2/2015 | Vedantham et al. |
| 2015/0055745 A1 | 2/2015 | Holzner et al. |
| 2015/0092924 A1 | 4/2015 | Yun et al. |
| 2015/0110252 A1 | 4/2015 | Yun et al. |
| 2015/0117599 A1 | 4/2015 | Yun et al. |
| 2015/0194287 A1 | 7/2015 | Yun et al. |
| 2015/0243397 A1 | 8/2015 | Yun et al. |
| 2015/0247811 A1 | 9/2015 | Yun et al. |
| 2015/0260663 A1 | 9/2015 | Yun et al. |
| 2015/0357069 A1 | 12/2015 | Yun et al. |
| 2016/0064175 A1 | 3/2016 | Yun et al. |
| 2016/0066870 A1 | 3/2016 | Yun et al. |
| 2016/0106387 A1 | 4/2016 | Kahn et al. |
| 2016/0178540 A1 | 6/2016 | Yun et al. |
| 2016/0268094 A1 | 9/2016 | Yun et al. |
| 2016/0320320 A1 | 11/2016 | Yun et al. |
| 2016/0351370 A1 | 12/2016 | Yun et al. |
| 2017/0047191 A1 | 2/2017 | Yun et al. |
| 2017/0052128 A1 | 2/2017 | Yun et al. |
| 2017/0162288 A1 | 6/2017 | Yun et al. |
| 2017/0162359 A1 | 6/2017 | Tang et al. |
| 2017/0227476 A1 | 8/2017 | Zhang et al. |
| 2017/0234811 A1 | 8/2017 | Zhang et al. |
| 2017/0261442 A1 | 9/2017 | Yun et al. |
| 2017/0336334 A1 | 11/2017 | Yun et al. |
| 2018/0144901 A1 | 5/2018 | Yun et al. |
| 2018/0261352 A1 | 9/2018 | Matsuyama et al. |
| 2018/0306734 A1 | 10/2018 | Morimoto et al. |
| 2018/0323032 A1 | 11/2018 | Strelec et al. |
| 2018/0344276 A1 | 12/2018 | DeFreitas et al. |
| 2018/0348151 A1 | 12/2018 | Kasper et al. |
| 2018/0356355 A1 | 12/2018 | Momose et al. |
| 2019/0017942 A1 | 1/2019 | Filevich. |
| 2019/0017946 A1 | 1/2019 | Wack et al. |
| 2019/0018824 A1 | 1/2019 | Zarkadas |
| 2019/0019647 A1 | 1/2019 | Lee et al. |

(56) References Cited

U.S. PATENT DOCUMENTS

| | | |
|---|---|---|
| 2019/0027265 A1 | 1/2019 | Dey et al. |
| 2019/0043689 A1 | 2/2019 | Camus |

FOREIGN PATENT DOCUMENTS

| | | |
|---|---|---|
| EP | 0432568 | 6/1991 |
| EP | 0751533 | 1/1997 |
| EP | 1028451 | 8/2000 |
| FR | 2548447 | 1/1985 |
| JP | H06-188092 | 7/1994 |
| JP | H07-056000 | 3/1995 |
| JP | H08-184572 | 7/1996 |
| JP | 2000-306533 | 11/2000 |
| JP | 2003-288853 | 10/2003 |
| JP | 2004-089445 | 3/2004 |
| JP | 2007-218683 | 8/2007 |
| JP | 2007-265981 | 10/2007 |
| JP | 2007-311185 | 11/2007 |
| JP | 2008-200359 | 4/2008 |
| JP | 2008-145111 | 6/2008 |
| JP | 2008-197495 | 8/2008 |
| JP | 2009-195349 | 3/2009 |
| JP | 2009-212058 | 9/2009 |
| JP | 2010-236986 | 10/2010 |
| JP | 2011-029072 | 2/2011 |
| JP | 2011-218147 | 11/2011 |
| JP | 2012-032387 | 2/2012 |
| JP | 2012-187341 | 10/2012 |
| JP | 2012-254294 | 12/2012 |
| JP | 2013-508683 | 3/2013 |
| JP | 2013-157269 | 8/2013 |
| JP | 2013-160637 | 8/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |
| WO | WO 2006/096052 | 9/2006 |
| WO | WO 2007/1125833 | 11/2007 |
| WO | WO 2009/098027 | 8/2009 |
| WO | WO 2009/1104560 | 8/2009 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/031740 | 3/2017 |
| WO | WO 2017/204850 | 11/2017 |
| WO | WO 2017/213996 | 12/2017 |
| WO | WO 2018/175570 | 9/2018 |

OTHER PUBLICATIONS

"Element Six CVD Diamond Handbook" (Element Six, Luxembourg, 2015).
"High performance benchtop EDXRF spectrometer with Windows® software," published by: Rigaku Corp., Tokyo, Japan; 2017.
"Monochromatic Doubly Curved Crystal Optics," published by: X-Ray Optical Systems, Inc. (XOS), East Greenbush, NY; 2017.
"Optics and Detectors," Section 4 of XS-Ray Data Booklet, 3rd Ed., A.C. Thompson ed. (Lawrence Berkeley Nat'l Lab, Berkeley, CA, 2009).
"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.
"Science and Technology of Future Light Sources", Arthur L. Robinson (LBNL) and Brad Plummer (SLAG), eds. Report Nos. ANL-08/39 / BNL-81895-2008 / LBNL-1090E-2009 / SLAC-R-917 (Lawrence Berkeley Nal'l Lab, Berkeley, CA, Dec. 2008).
"Series 5000 Packaged X-ray Tubes," Product Technical Data Sheet DS006 Rev. G, X-Ray Technologies Inc. (Oxford Insstruments), Scotts Valley, CA (no date).
"Toward Control of Matter: Energy Science Needs for a New Class of X-Ray Light Sources" (Lawrence Berkeley Nal'l Lab, Berkeley, CA, Sep. 2008).
"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).
Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.
Adachi et al., "Development of the 17-inch Direct-Conversion Dynamic Flat-panel X-ray Detector (FPD)," Digital R/F (Shimadzu Corp., 2 pages (no date, published -2004 with product release).
Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition" , (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).
Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., Focusing Mirrors for Use with Microfocus X-ray Tubes, 1998, Journal of Applied Crystallography, vol. 31, pp. 733-741.
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.
Bech, "In-vivo dark-field and phase-contrast x-ray imaging," Scientific Reports 3, (2013), Article No. 03209.
Bech, "X-ray imaging with a grating interferometer," University of Copenhagan PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.

(56) References Cited

OTHER PUBLICATIONS

Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.

Bilderback et al., "Single Capillaries," Ch. 29 of "Handbook of Optics vol. III, 2nd Ed." (McGraw Hill, New York, 2001).

Birkholz, "Chapter 4: Grazing Incidence Configurations," Thin Film Analysis by X-ray Scattering (Wiley-VCH Verlag GmbH & Co. KGaA, Weinheim, Germany, 2006).

Bjeoumikhov et al., "A modular system for XRF and XRD applications consisting of a microfocus X-ray source and different capillary optics," X-ray Spectrometry, vol. 33 (2004), pp. 312-316.

Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.

Canberra Model S-5005 WinAxil X-Ray Analysis Software, published by: Canberra Eurisys Benelux N.V./S.A.,Zellik, Belgium; Jun. 2004.

Cerrina, "The Schwarzschild Objective," Ch. 27 of "Handbook of Optics vol. III, 2nd Ed." (McGraw Hill, New York, 2001).

Chen et al., "Advance in detection of low sulfur content by wavelength dispersive XRF," Proceedings of the Annual ISA Analysis Division Symposium (2002).

Chen et al., "Doubly curved crystal (DCC) X-ray optics and applications," Powder Diffraction, vol. 17(2) (2002), pp. 99-103.

Chen et al., "Guiding and focusing neutron beams using capillary optics," Nature vol. 357 (Jun. 4, 1992), pp. 391-393.

Chervenak et al., "Experimental thick-target bremsstrahlung spectra from electrons in the range 10 to 30 keV", Phys. Rev. A vol. 12 (1975), pp. 26-33.

Coan et al., "In vivo x-ray phase contrast analyzer-based imaging for longitudinal osteoarthritis studies in guinea pigs," Phys. Med. Biol. vol. 55(24) (2010), pp. 7649-7662.

Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).

Cohen et al., "Tunable laboratory extended x-ray absorption fine structure system," Rev. Sci. Instr. vol. 51, No. 3, Mar. 1980, pp. 273-277.

Cong et al., "Fourier transform-based iterative method for differential phase-contrast computed tomography", Opt. Lett. vol. 37 (2012), pp. 1784-1786.

Cornaby et al., "Advances in X-ray Microfocusing with Monocapillary Optics at CHESS," CHESS News Magazine (2009), pp. 63-66.

Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.

Cornaby, "The Handbook of X-ray Single Bounce Monocapillary Optics, Including Optical Design and Synchrotron Applications" (PhD Dissertation, Cornell University, Ithaca, NY, May 2008).

David et al., "Fabrication of diffraction gratings for hard x-ray phase contrast imaging," Microelectron. Eng. vol. 84, (2007), pp. 1172-1177.

David et al., "Hard X-ray phase imaging and tomography using a grating interferometer," Spectrochimica Acta Part B vol. 62 (2007) pp. 626-630.

Davis et al., "Bridging the Micro-to-Macro Gap: A New Application for Micro X-Ray Fluorescence," Microsc Microanal., vol. 17(3) (Jun. 2011), pp. 410-417.

Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628-635 (9 pages). Jun. 18, 2010.

Ding et al., "Reactive Ion Etching of CVD Diamond Films for MEMS Applications," Micromachining and Microfabrication, Proc. SPIE vol. 4230 (2000), pp. 224-230.

Dobrovinskaya et al., "Thermal Properties," Sect. 2.1.5 of "Sapphire: Material, Manufacturing,, Applications" (Springer Science + Business Media, New York, 2009).

Erko et al., "X-ray Optics," Ch. 3 of "Handbook of Practical X-Ray Fluorescence Analysis," B. Beckhoff et al., eds. (Springer, Berlin, Germany, 2006), pp. 85-198.

Falcone et al., "New directions in X-ray microscopy," Contemporary Physics, vol. 52, No. 4, (Jul.-Aug. 2010), pp. 293-318.

Fernández-Ruiz, "TXRF Spectrometry as a Powerful Tool for the Study of Metallic Traces in Biological Systems," Development in Analytical Chemistry, vol. 1 (2014), pp. 1-14.

Freund, "Mirrors for Synchrotron Beamlines," Ch. 26 of "Handbook of Optics vol. III, 2nd Ed." (McGraw Hill, New York, 2001).

Ge et al., "Investigation of the partially coherent effects in a 2D Talbot interferometer," Anal. Bioanal. Chem. vol. 401, (2011), pp. 865-870. Apr. 29, 2011 pub Jun. 14, 2011.

Gibson et al., "Polycapillary Optics: An Enabling Technology for New Applications," Advances in X-ray Analysis, vol. 45 (2002), pp. 286-297.

Gonzales et al., "Angular Distribution of Bremsstrahlung Produced by 10-Kev and 20 Kev Electrons Incident on a Thick Au Target", in Application of Accelerators in Research and Industry, AIP Conf. Proc. 1221 (2013), pp. 114-117.

Gonzales et al., "Angular distribution of thick-target bremsstrahlung produced by electrons with initial energies ranging from 10 to 20 keV incident on Ag", Phys. Rev. A vol. 84 (2011): 052726.

Guttmann et al., "Ellipsoidal capillary as condenser for the BESSSY full-field x-ray microscope," J. Phys. Conf. Ser. vol. 186 (2009): 012064.

Harasse et al., "Iterative reconstruction in x-ray computed laminography from differential phase measurements", Opt. Express. vol. 19 (2011), pp. 16560-16573.

Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.

Harasse et al., "X-ray Phase Laminography with Talbot Interferometer", in Developments in X-Ray Tomography VII, Proc. SPIE vol. 7804 (2010), 780411.

Hasse et al., "New developments in laboratory-based x-ray sources and optics," Adv. In Laboratory-based X-Ray Sources, Optics, and Applications VI, ed. A.M. Khounsary, Proc. SPIE vol. 10387, 103870B-1 (2017).

Hemraj-Benny et al., "Near-Edge X-ray Absorption Fine Structure Spectroscopy as a Tool for Investigating Nanomaterials," Small, vol. 2(1), (2006), pp. 26-35.

Henke et al., "X-ray interactions: photoabsorption, scattering, transmission, and reflection at E=50-30000 eV, Z=1-92," Atomic Data and Nuclear Data Tables, vol. 54 (No. 2) (Jul. 1993), pp. 181-342.

Honma et al., Full-automatic XAFS Measurement System of the Engineering Science Research II beamline BL14B2 at Spring-8, 2011, AIP Conference Proceedings 1234, pp. 13-16.

Howard et al., "High-Definition X-ray Fluorescence Elemental Mapping of Paintings," Anal. Chem., 2012, vol. 84(7), pp. 3278-3286.

Howells, "Gratings and Monochromators in the VUV and Soft X-RAY Spectral Region," Ch. 21 of Handbook of Optics vol. III, 2nd Ed. (McGraw Hill, New York, 2001).

Howells, "Mirrors for Synchrotron-Radiation Beamlines," Publication LBL-34750 (Lawrence Berkeley Laboratory, Berkeley, CA, Sep. 1993).

Hrdý et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).

Hwang et al, "New etching process for device fabrication using diamond," Diamond & Related Materials, vol. 13 (2004) pp. 2207-2210.

Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.

(56) References Cited

OTHER PUBLICATIONS

Ihsan et al., "A microfocus X-ray tube based on a microstructured X-ray target", Nuclear Instruments and Methods in Physics Research B vol. 267 (2009) pp. 3566-3573.
Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable In-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jiang et al., "X-Ray Phase-Contrast Imaging with Three 2D Gratings," Int. J. Biomed. Imaging, (2008), 827152, 8 pages.
Joy, "Astronomical X-ray Optics," Ch. 28 of "Handbook of Optics vol. III, 2nd Ed.," (McGraw Hill, New York, 2001).
Keyrilainen et al., "Phase contrast X-ray imaging of breast," Acta Radiologica, vol. 51 (8), (2010), pp. 866-884. Jan. 18, 2010 pub Jun. 15, 2010.
Kidalov et al., "Thermal Conductivity of Diamond Composites," Materials, vol. 2 (2009) pp. 2467-2495.
Kido et al., "Bone Cartilage Imaging with X-ray Interferometry using a Practical X-ray Tube", in Medical Imaging 2010: Physics of Medical Imaging, Proc. SPIE vol. 7622 (2010), 762240.
Kim, "Talbot images of wavelength-scale amplitude gratings," Opt. Express vol. 20(5), (2012), pp. 4904-4920.
Kirkpatrick et al., "Formation of Optical Images by X-Rays", J. Opt. Soc. Am. vol. 38(9) (1948), pp. 766-774.
Kirz, "Phase zone plates for x rays and the extreme uv," J. Op. Soc. Am. vol. 64 (Mar. 1974), pp. 301-309.
Kirz et al., "The History and Future of X-ray Microscopy", J. Physics: Conden. Series vol. 186 (2009): 012001.
Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.
Kottler et al., "Dual energy phase contrast x-ray imaging with Talbot-Lau interferometer," J. Appl. Phys. vol. 108(11), (2010), 114906. Jul. 7, 2010 pub Dec. 7, 2010.
Kumakhov et al., "Multiple reflection from surface X-ray optics," Physics Reports, vol. 191(5), (1990), pp. 289-350.
Kumakhov, "X-ray Capillary Optics. History of Development and Present Status" in Kumakhov Optics and Application, Proc. SPIE 4155 (2000), pp. 2-12.
Kuwabara et al., "Hard-X-ray Phase-Difference Microscopy with a Low-Brilliance Laboratory X-ray Source", Appl. Phys. Express vol. 4 (2011) 062502.
Kuznetsov, "X-Ray Optics Calculator," Institute of Microelectronics Technology and High Purity Materials, Russian Academy of Sciences (IMT RAS), Chernogolovka, Russia (6 pages submitted); 2016.
Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.
Lai, "X-Ray Microfocusing Optics," Slide Presentation from Argonne National Laboratory, 71 slides, Cheiron Summer School 2007.

Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.
Lechner et al., "Silicon drift detecors for high count rate X-ray spectroscopy at room temperature," Nuclear Instruments and Methods, vol. 458A (2001), pp. 281-287.
Leenaers et al., "Application of Glancing Incidence X-ray Analysis," 1997, X-ray Spectrometry, vol. 26, pp. 115-121.
Lengeler et al., "Refractive X-ray Optics," Ch. 20 of "Handbook of Optics vol. III, 2nd Ed." (McGraw Hill, New York, 2001).
Li et al., "Source-optic-crystal optimisation for compact monochromatic imaging," Proc. SPIE 5537 (2004), pp. 105-114.
Lohmann et al., "An interferometer based on the Talbot effect," Optics Communications vol. 2 (1971), pp. 413-415.
MacDonald et al., "An Introduction to X-ray and Neutron Optics," Ch. 19 of "Handbook of Optics vol. III, 2nd Ed." (McGraw Hill, New York, 2001).
MacDonald et al., "Polycapillary and Multichannel Plate X-Ray Optics," Ch. 30 of "Handbook of Optics vol. III, 2nd Ed.," (McGraw Hill, New York, 2001).
MacDonald et al., "Polycapillary X-ray Optics for Microdiffraction," J. Appl. Cryst., vol. 32 (1999) pp. 160-167.
MacDonald, "Focusing Polycapillary Optics and Their Applications," X-Ray Optics and Instrumentation, vol. 2010, (Oct. 2010): 867049.
Maj et al., "Etching methods for improving surface imperfections of diamonds used for x-ray monochromators," Adv. X-ray Anal., vol. 48 (2005), pp. 176-182.
Malgrange, "X-ray Optics for Synchrotron Radiation," ACTA Physica Polinica A, vol. 82(1) (1992) pp. 13-32.
Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.
Matsushita, "Mirrors and Multilayers," Slide Presentation from Photon Factor, Tsukuba, Japan, 65 slides, (Cheiron School 2009, Sprint-8, Japan, Nov. 2009).
Matsushita, "X-ray monochromators," Slide Presentation from Photon Factory, Tsukuba, Japan, 70 slides, (Cheiron School 2009, Spring-8, Japan, Nov. 2009).
Matsuyama et al., "Wavefront measurement for a hard-X-ray nanobeam using single-grating interferometry", Opt Express vol. 20 (2012), pp. 24977-24986.
Miao et al., "Motionless phase stepping in X-ray phase contrast imaging with a compact source," Proceedings of the National Academy of Sciences, vol. 110(48), (2013), pp. 19268-19272.
Michette, "Zone and Phase Plates, Bragg-Fresnel Optics," Ch. 23 of "Handbook of Optics vol. III, 2nd Ed.," (McGraw Hill, New York, 2001).
Mizutani et al., X-ray microscopy for neural circuit reconstruction in 9th International Conference on X-Ray Microscopy, J. Phys: Conf. Ser. 186 (2009) 012092.
Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.
Momose et al., "Biomedical Imaging by Talbot-Type X-Ray Phase Tomography" in Developments in X-Ray Tomography V, Proc. SPIE vol. 6318 (2006) 63180T.
Momose et al., "Grating-Based X-ray Phase Imaging Using Multiline X-ray Source", Jpn. J. Appl. Phys. vol. 48 (2009), 076512.
Momose et al., "Phase Tomography by X-ray Talbot Interferometry for Biological Imaging" Jpn. J. Appl. Phys. vol. 45 2006 pp. 5254-5262.
Momose et al., "Phase Tomography Using X-ray Talbot Interferometer", in Synchrotron Radiation Instrumentation: Ninth International Conference, AIP Conf. Proc. vol. 879 (2007), pp. 1365-1368.
Momose et al., "Phase-Contrast X-Ray Imaging Using an X-Ray Interferometer for Biological Imaging", Analytical Sciences vol. 17 Supplement (2001), pp. i527-i530.
Momose et al., "Sensitivity of X-ray Phase Imaging Based on Talbot Interferometry", Jpn. J. Appl. Phys. vol. 47 (2008), pp. 8077-8080.
Momose et al., "X-ray Phase Measurements with Talbot Interferometry and Its Applications", in International Conference on Advanced

(56) References Cited

OTHER PUBLICATIONS

Phase Measurement Methods in Optics and Imaging, AIP Conf. Proc. vol. 1236 (2010), pp. 195-199.
Momose et al., "X-ray Phase Imaging—From Static Observation to Dynamic Observation—", in International Workshop on X-ray and Neutron Phase Imaging with Gratings AIP Conf. Proc. vol. 1466, (2012), pp. 67-77.
Momose et al., "X-ray Phase Imaging Using Lau Effect", Appl. Phys. Express vol. 4 (2011) 066603.
Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "X-ray Talbot Interferometry with Capillary Plates", Jpn. J. Appl. Phys. vol. 45 (2006), pp. 314-316.
Momose et al., "Four-dimensional X-ray phase tomography with Talbot interferometry and white synchrotron radiation: dynamic observation of a living worm", Opt. Express vol. 19 (2011), pp. 8423-8432.
Momose et al., "High-speed X-ray phase imaging and X-ray phase tomography with Talbot interferometer and white synchrotron radiation", Opt. Express vol. 17 (2009), pp. 12540-12545.
Momose et al., "Phase Imaging with an X-ray Talbot Interferometer", Advances in X-ray Analysis vol. 49(3) (2006), pp. 21-30.
Momose et al.,"Demonstration of X-Ray Talbot Interferometry", Jpn. J. Appl. Phys. vol. 42 (2003), pp. L866-L868.
Momose et al.,"Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Montgomery, "Self Imaging Objects of Infinite Aperture," J. Opt. Soc. Am. vol. 57(6), (1967), pp. 772-778.
Morimoto et al., "Development of multiline embedded X-ray targets for X-ray phase contrast imaging," XTOP 2012 Book of Abstracts, (Ioffe Physical-Technical Institute of the Russian Academy of Sciences, St. Petersburg, Russia, 2012), pp. 74-75.
Morimoto et al., X-ray phase contrast imaging by compact Talbot-Lau interferometer with a signal transmission grating, 2014, Optics Letters, vol. 39, No. 15, pp. 4297-4300.
Munro et al., Design of a novel phase contrast imaging system for mammography, 2010, Physics in Medicine and Biology, vol. 55, No. 14, pp. 4169-4185.
Nango et al., "Talbot-defocus multiscan tomography using the synchrotron X-ray microscope to study the lacuno-canalicular network in mouse bone", Biomed. Opt. Express vol. 4 (2013), pp. 917-923.
Neuhausler et al., "Non-destructive high-resolution X-ray imaging of ULSI micro-electronics using keV X-ray microscopy in Zernike phase contrast," Microelectronic Engineering, Elsevier Publishers Bv., Amsterdam, NO, vol. 83, No. 4-9 (Apr. 1, 2006) pp. 1043-1046.
Newville, "Fundamentals of XAFS," (Univ. of Chicago, Chicago, IL, Jul. 23, 2004).
Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.
Noda et al., "Fabrication of High Aspect Ratio X-ray Grating Using X-ray Lithography" J. Solid Mech_Mater. Eng. vol. 3 (2009), pp. 416-423.
Nojeh, "Carbon Nanotube Electron Sources: From Electron Beams to Energy Conversion and Optophononics", ISRN Nanomaterials vol. 2014 (2014): 879827.
Nuhn, "From storage rings to free electron lasers for hard x-rays", J.A37 Phys.: Condens. Matter vol. 16 (2004), pp. S3413-S34121.

Nykanen et al., "X-ray scattering in full-field digital mammography," Med. Phys. vol. 30(7), (2003), pp. 1864-1873.
Oji et al., Automatic XAFS measurement system developed at BL14B2 in SPring-8, Available online Nov. 15, 2011, Journal of Synchrotron Radiation, vol. 19, pp. 54-59.
Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-6S658.
Otendal et al., A 9 keV electron-impact liquid-gallium-jet x-ray source', Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
PAXSCAN Flat Panel X-ray Imaging, Varian Sales Brochure, (Varian Medical Systems, Palo Alto, CA, Nov. 11, 2004).
Pfeiffer et al., " Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382 (equation quoted from p. 336).
Prewitt et al., "FIB Repair of 5X Recticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (Cern, Geneva, Switzerland, Jul. 1993).
Röntgen, Ueber eine neue Art von Strahlen (Wurzburg Verlag, Warzburg, Germany, 1896) also, in English, "On a New Kind of Rays," Nature vol. 53 (Jan. 23 1896). pp. 274-276.
Rovezzi, "Study of the local order around magnetic impurities in semiconductors for spintronics." PhD Dissertation, Condensed Matter, UniversitéJoseph-Fourier—Grenoble I, 2009, English <tel-00442852>.
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS ONE, vol. 9, Issue 5 (May 2014) e93502.
Scholz, "X-ray Tubes and Monochromators," Technical Workshop EPIV, Universität Würzburg (2007); 41 slides, 2007.

(56) References Cited

OTHER PUBLICATIONS

Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germay, 2006), pp. 85-198.
Sebert, "Flat-panel detectors:how much better are they?" Pediatr. Radiol. vol. 36 (Suppl 2), (2006), pp. 173-181.
Shen, "Polarizing Crystal Optics," Ch. 25 of "Handbook of Optics vol. III, 2nd Ed.," (McGraw Hill, New York, 2001).
Shields et al., "Overview of Polycapillary X-ray Optics," Powder Diffraction, vol. 17(2) (Jun. 2002), pp. 70-80.
Shimura et al., "Hard x-ray phase contrast imaging using a tabletop Talbot-Lau interferometer with multiline embedded x-ray targets", Opt. Lett. vol. 38(2) (2013), pp. 157-159.
Siddons, "Crystal Monochromators and Bent Crystals," Ch. 22 of "Handbook of Optics vol. III, 2nd Ed.," (McGraw Hill, New York, 2001).
Smith, "Fundamentals of Digital Mammography:Physics, Technology and Practical Considerations," Publication R-BI-016 (Hologic, Inc., Bedford, MA, Mar. 2005).
Snigirev et al., "Hard X-Ray Microoptics," Ch. 17 of "Modern Developments in X-Ray and Neutron Optics," A. Erko et al., eds (Springer, Berlin, Germany, 2008), pp. 255-285.
Sparks JR., "X-ray Fluorescence Microprobe for Chemical Analysis," in Synchrotron Radiation Research, H. Winick & S. Doniach, eds. (Plenum Press, New York, NY 1980), pp. 459-512.
Spiller, "Multilayers," Ch. 24 of "Handbook of Optics vol. III, 2nd Ed.," (McGraw Hill, New York, 2001).
Stampanoni et al., "The First Analysis and Clinical Evaluation of Native Breast Tissue Using Differential Phase-Contrast Mammography," Investigative Radiology, vol. 46, pp. 801-806. pub 2011-12-xx.
Strüder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentations/Strueder.pdf>.
Suzuki et al., "Hard X-ray Imaging Microscopy using X-ray Guide Tube as Beam Condenser for Field Illumination," J. Phys.: Conf. Ser. vol. 463 (2013): 012028.
Suzuki, "Development of the DIGITEX Safire Cardiac System Equipped with Direct conversion Flat Panel Detector," Digital Angio Technical Report (Shimadzu Corp., Kyoto, Japan, no date, published—2004 with product release).
Takahama, "RADspeed safire Digital General Radiography System Equipped with New Direct—Conversion FPD," Medical Now, No. 62 (2007).
Takeda et al., "Differential Phase X-ray Imaging Microscopy with X-ray Talbot Interferometer". Appl. Phys. Express vol. 1 (2008) 117002.
Takeda et al., "X-Ray Phase Imaging with Single Phase Grating", Jpn. J. Appl. Phys. vol. 46 (2007), pp. L89-L91.
Takeda et al., "In vivo physiological saline-infused hepatic vessel imaging using a two-crystal-interferometer-based phase-contrast X-ray technique", J. Synchrotron Radiation vol. 19 (2012), pp. 252-256.
Talbot, "Facts relating to optical science No IV," Philos. Mag. vol. 9 (1836), pp. 401-407.
Tanaka et al., "Cadaveric and in vivo human joint imaging based on differential phase contrast by X-ray Talbot-Lau interferometry", Z. Med. Phys. vol. 23 (2013), pp. 222-227.
Tang et al., "Micro-computed tomography (Micro-CT): a novel appraoch for intraoperative breast cancer specimen imaging," Breast Cancer Res. Treat. vol. 139, pp. 311-316 (2013).
Taniguchi et al., "Diamond nanoimprint lithography," Nanotechnology, vol. 13 (2002) pp. 592-596.
Tkachuk et al., "High-resolution x-ray tomography using laboratory sources", in Developments in X-Ray Tomography V, Proc. SPIE 6318 (2006): 631810.

Tkachuk et al., "Multi-length scale x-ray tomography using laboratory and synchrotron sources", Microsc. Microanal. vol. 13 (Suppl. 2) (2007), pp. 1570-1571.
Touzelbaev et al., "Applications of micron-scale passive diamond layers for the integrated circuits and microelectromechanical systems industries," Diamond and Rel. Mat'ls, vol. 7 (1998) pp. 1-14.
Tsuji et al., "X-Ray Spectrometry: Recent Technological Acvances," John Wiley & Sons Ltd. Chichester, West Susses, UK 2004), Chapters 1-7.
Udagawa, "An Introduction to In-House EXAFS Facilities," The Rigaku Journal, vol. 6, (1) (1989), pp. 20-27.
Udagawa, "An Introduction to X-ray Absorption Fine Structure," The Rigaku Journal, vol. 11(2)(1994), pp. 30-39.
Uehara et al., "Effectiveness of X-ray grating interferometry for non-destructive inspection of packaged devices", J. Appl. Phys. vol. 114 (2013), 134901.
Vogt, "X-ray Fluorescence Microscopy: A Tool for Biology, Life Science and Nanomedicine," Presentation on May 16, 2012 at James Madison Univ., Harrisonburg, VA (31 slides), 2012.
Wan et al.,"Fabrication of Multiple Slit Using Stacked-Sliced Method for Hard X-ray Talbot—Lau Interferometer", Jpn. J. Appl. Phys. vol. 47 (2008), pp. 7412-7414.
Wang et al., "Advantages of intermediate X-ray energies in Zernicke phase constrast X-ray microscopy," Biotech. Adv., vol. 31 (2013) pp. 387-392.
Wang et al., "Non-invasive classification of microcalcifications with phase-contrast X-ray mammography," Nature Comm. vol. 5:3797, pp. 1-9 (2014).
Wang, On the single-photon-counting (SPC) modes of imaging using an XFEL source, presented at IWORLD2015.
Wang et al., "Precise patterning of diamond films for MEMS application" Journal of Materials Processing Technology vol. 127 (2002), pp. 230-233.
Weitkamp et al., "Design aspects of X-ray grating interferometry," in International Workshop on X-ray and Neutron Phase Imaging with Gratings AIP Conf. Proc. vol. 1466, (2012), pp. 84-89.
Weitkamp et al., "Hard X-ray phase imaging and tomography with a grating interferometer," Proc. SPIE vol. 5535, (2004), pp. 137-142.
Weitkamp et al., "X-ray wavefront diagnostics with Talbot interferometers," International Workshop on X-Ray Diagnostics and Scientific Application of the European XFEL, Ryn, Poland, (2010), 36 slides.
Weitkamp et al., Tomography with grating interferometers at low-brilliance sources, 2006, SPIE, vol. 6318, pp. 0S-1 to 0S-10.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wobrauschek et al., "Energy Dispersive, X-Ray Fluorescence Analysis," Encyclopedia of Analytical Chemistry, R.A. Meyers, Ed. (Wiley 2010).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.
Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.
X-ray-Optics.de Website, http://www.x-ray-optics.de/, accessed Feb. 13, 2016.
Yakimchuk et al., "Ellipsoidal Concentrators for Laboratory X-ray Sources: Analytical approaches for optimization," Mar. 22, 2013, Crystallography Reports, vol. 58, No. 2, pp. 355-364.
Yamamoto, "Fundamental physics of vacuum electron sources", Reports on Progress in Physics vol. 69, (2006), pp. 181-232.

(56) References Cited

OTHER PUBLICATIONS

Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.

Yang et al., "Analysis of Intrinsic Stress in Diamond Films by X-ray Diffraction," Advances in X-ray Analysis, vol. 43 (2000), pp. 151-156.

Yashiro et al., "Distribution of unresolvable anisotropic microstructures revealed in visibility-contrast images using x-ray Talbot interferometry", Phys. Rev. B vol. 84 (2011), 094106.

Yashiro et al., "Hard x-ray phase-imaging microscopy using the self-imaging phenomenon of a transmission grating", Phys. Rev. A vol. 82 (2010), 043822.

Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.

Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.

Yashiro et al., "Efficiency of capturing a phase image using cone-beam x-ray Talbot interferometry", J. Opt. Soc. Am. A vol. 25 (2008), pp. 2025-2039.

Yashiro et al., "On the origin of visibility contrast in x-ray Talbot interferometry", Opt. Express (2010), pp. 16890-16901.

Yashiro et al., 'Optimal Design of Transmission Grating for X-ray Talbot Interferometer, Advances in X-ray Analysis vol. 49(3) (2006), pp. 375-379.

Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.

Yashiro et. al., "Hard-X-Ray Phase-Difference Microscopy Using a Fresnel Zone Plate and a Transmission Grating", Phys. Rev. Lett. vol. 103 (2009), 180801.

Yu et al., "Morphology and Microstructure of Tungsten Films by Magnetron Sputtering," Mat. Sci. Forum, vol. 913, pp. 416-423 (2018).

Zanette et al., "Two-Dimensional X-Ray Grating interferometer," Phys. Rev. Lett. vol. 105 (2010) pp. 248102-1 248102-4.

Zeng et al., "Ellipsoidal and parabolic glass capillaries as condensers for x-ray microscopes," Appl. Opt. vol. 47 (May 2008), pp. 2376-2381.

Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.

Zhang et al., "Fabrication of Diamond Microstructures by Using Dry and Wet Etching Methods", Plasma Science and Technology vol. 15(6) (Jun. 2013), pp. 552-554.

Dong et al., "Improving Molecular Sensitivity in X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).

Hennekam et al., "Trace metal analysis of sediment cores using a novel X-ray fluorescence core scanning method," Quaternary Int'l, https://dol.org/10.1016/j.quaint.2018.10.018 (2018).

Malzer et al., "A laboratory spectrometer for high throughput X-ray emission spectroscopy in catalysis research," Rev. Sci. Inst. 89, 113111 (2018).

Viermetz et al., "High resolution laboratory grating-based X-ray phase-contrast CT," Scientific Reports 8:15884 (2018).

International Search Report and Written Opinion in PCT/US2018/023547 dated Aug. 3, 2018 in 14 pages.

Jahrman et al., "Vacuum formed temporary spherically and toroidally bent crystal analyzers for x-ray absorption and x-ray emission spectroscopy," Rev. Sci. Inst. vol. 90, 013106 (2019).

Li et al., "X-ray phase-contrast imaging using cascade Talbot-Lau interferometers," Proc. SPIE 10964 (2018), pp. 1096469-1-1096469-6.

Lühl et al., "Scanning transmission X-ray microscopy with efficient X-ray fluorescence detection (STXM-XRF) for biomedical applications in the soft and tender energy range," J. Synch. Rad. vol. 26, https://doi.org/10.1107/S1600577518016879, (2019).

Scott, "Hybrid Semiconductor Detectors for High Spatial Resolution Phase-contrast X-ray Imaging," Thesis, University of Waterloo, Department of Electrical and Computer Engineering, 2019.

Sun et al., "Combined optic system based on polycapillary X-ray optics and single-bounce monocapillary optics for focusing X-rays from a conventional laboratory X-ray source," Nucl. Inst. and Methods in Phys. Res. A 802 (2015) pp. 5-9.

Sun et al., "Numerical design of in-line X-ray phase-contrast imaging based on ellipsoidal single-bounce monocapillary," Nucl. Inst. and Methods in Phys. Res. A746 (2014) pp. 33-38.

Sunday et al., "X-ray Metrology for the Semiconductor Industry Tutorial," J. Res. Nat'l Inst. Stan. vol. 124: 124003 (2019); https://doi.org/10.6028/jres.124.003.

Töpperwien et al., "Multiscale x-ray phase-contrast tomography in a mouse model of transient focal cerebral ischemia," Biomed. Op. Express, vol. 10, No. 1, Jan. 2019, pp. 92-103.

Zhang et al., "Application of confocal X-ray fluorescence based on capillary X-ray optics in nondestructively measuring the inner diameter of monocapillary optics," Optics Comm. (2018) https://doi.org/10.1016/j.optcom.2018.11.064.

Zhang et al., "Measurement of the inner diameter of monocapillary with confocal X-ray scattering technology based on capillary X-ray optics," Appl. Opt. (Jan. 8, 2019), doc ID 351489, pp. 1-10.

\* cited by examiner

METHOD OF PERFORMING X-RAY SPECTROSCOPY AND X-RAY ABSORPTION SPECTROMETER SYSTEM

CROSS-REFERENCE TO RELATED APPLICATIONS

This Patent Application claims the priority benefit of provisional patent application No. 62/475,213, filed Mar. 22, 2017, is a Continuation-in-Part of U.S. patent application Ser. No. 15/431,786, filed Feb. 14, 2017, which in turn is a Continuation-in-Part of U.S. patent application Ser. No. 15/269,855, filed Sep. 19, 2016 now issued as U.S. Pat. No. 9,570,265, and is also a Continuation-in-Part of U.S. patent application Ser. No. 15/166,274, filed May 27, 2016, all of which are hereby incorporated by reference in their entirety. Additionally, U.S. patent application Ser. No. 15/269,855 is a Continuation-in-Part of U.S. patent application Ser. No. 14/544,191, filed Dec. 5, 2014 and now issued as U.S. Pat. No. 9,449,781, which is hereby incorporated by reference in its entirety, and which claims the benefit of U.S. Provisional Patent Application Nos. 61/912,478, filed on Dec. 5, 2013, 61/912,486, filed on Dec. 5, 2013, 61/946,475, filed on Feb. 28, 2014, and 62/008,856, filed on Jun. 6, 2014, all of which are incorporated herein by reference in their entirety. Application Ser. No. 15/269,855 is also a Continuation-in-Part of U.S. patent application Ser. No. 14/636,994, filed Mar. 3, 2015 and now issued as U.S. Pat. No. 9,448,190, which is hereby incorporated by reference in its entirety, and which in turn claims the benefit of U.S. Provisional Patent Application Nos. 62/008,856, filed Jun. 6, 2014; 62/086,132, filed Dec. 1, 2014, and 62/117,062, filed Feb. 17, 2015, all of which are incorporated herein by reference in their entirety. Additionally, U.S. application Ser. No. 15/166,274 is a Continuation-in-Part of U.S. patent application Ser. No. 14/999,147, filed Apr. 1, 2016 and now issued as U.S. Pat. No. 9,543,109, which in turn claims the benefit of U.S. Provisional Patent Application Nos. 62/155,449 filed Apr. 30, 2015 and 62/141,847 filed Apr. 1, 2015; U.S. application Ser. No. 14/999,147is also a Continuation-in-Part of U.S. patent application Ser. No. 14/490,672 filed Sep. 19, 2014 and now issued as U.S. Pat. No. 9,390,881, which in turn claims the benefit of U.S. Provisional Patent Application Nos. 62/008,856 filed Jun. 6, 2014; 61/931,519 filed Jan. 24, 2014; 61/894,073 filed Oct. 22, 2013; and 61/880,151 filed Sep. 19, 2013, all of which are incorporated herein by reference in their entirety.

BACKGROUND

Field of the Invention

The embodiments of the invention disclosed herein relate to a method performing x-ray spectroscopy and an x-ray spectrometry systems having an x-ray illumination system comprising a focusing x-ray optic with an energy bandwidth greater than 10 eV that collects x-rays from the laboratory source and focuses portion of the collected x-rays on or near an object with a focus size less than 500 micrometers. In many embodiments, the focus spot is <10-20 um. Various embodiments of the spectrometer may have a variety of x-ray materials and optical elements to provide a variety of x-ray bandwidth ranges suitable for a variety of x-ray spectroscopy applications.

Discussion of Background

1. Introduction.

Measurement of the x-ray absorption properties of a material, especially near the ionization energy, can reveal information about the composition and chemical state of the material. X-ray absorption spectroscopy (XAS) is a technique commonly employed at high brightness synchrotron light sources for chemical analysis, but has been limited in its application at the laboratory due to a combination of the long acquisition times needed and poor spectral resolution of laboratory systems. To this end, a laboratory XAS system is described with significant innovations to increase the flux of x-rays at specific energies and achieve high spectral resolution to would allow better analysis of the absorption fine structure associated with the absorption edge.

To create such capabilities using laboratory x-ray sources, a new approach to x-ray absorption spectroscopy is required.

1.1 X-ray Source

Often laboratory sources of x-rays are created by bombarding an anode target having a selected x-ray generating material with electrons accelerated through a potential (measured in keV) in a vacuum. With the collision of the electrons and the material, there are several energy transfer mechanisms that can occur, including heat and the generation of x-rays. A spectrum of x-rays is produced with x-ray energies up to the original electron energy (in this example, about 50 KeV) which includes characteristic x-rays and continuum, often referred to as Bremsstrahlung radiation. Ways to increase the brightness of the x-ray source is to increase the energy of the electrons by raising the accelerating voltage, use a target material with a higher atomic number Z, and/or to increase the electron density bombarding the material. However, this is generally limited by the ability of the material to absorb energy without melting or damage. Therefore, most current art electron bombardment x-ray sources comprise a single x-ray radiating material with good thermal properties, such as a high melting point and high thermal conductivity. The target material may also be mounted onto, or embedded into, a substrate having properties selected to efficiently conduct heat away from the x-ray generating material, with the thickness of the x-ray generating material limited by the electron penetration depth.

1.2 X-Ray Focusing Optics.

X-rays generated by electron beam bombardment generally radiate in all directions and x-ray flux density on a sample for a given analysis area can be increased through the use of optics. For XAS measurement, the focusing optic needs to work for an energy bandwidth. In XAS embodiments thus far developed, x-ray optics have generally not used and instead a microfocus x-ray source is used.

1.3 X-Ray Absorption Spectrometer.

X-ray absorption spectroscopy (XAS) typically measures the fraction of x-rays absorbed by an object as a function of x-ray energy over a predetermined energy range with energy resolution better than 10 eV, inclusive an absorption edge of an element in the object. It is often carried out at synchrotron light sources because of their high brightness and easy energy tunability. Small laboratory-based x-ray absorption spectroscopy systems would provide easy access and full control; however the performance of laboratory XAS systems has been largely limited by a combination of many factors, including low brightness of the Bremsstrahlung radiation of laboratory x-ray sources, low diffraction efficiency of the crystal analyzer associated with the use of high index reflections, and non-optimal spectrometer design. Those limitations often result in unacceptably long acquisition times (~up to tens of hours) and/or poor energy resolution. As a consequence, there are few laboratory systems in use.

A recently developed in-laboratory system uses spherically bent crystal analyzers to achieve sufficiently high energy resolution for XANES measurement [Seidler, G. T., et al. "A modern laboratory XAFS cookbook." Journal of Physics: Conference Series. Vol. 712. No. 1. IOP Publishing, 2016]. However, that system has several limitations including: there is no focusing optic between the source and object, resulting in low x-ray flux density on the object; need of a large illuminated area to obtain sufficient x-ray flux on the object; as a consequence of the large illuminated area, crystal analyzers need to operate at high Bragg angles to achieve adequate energy resolution; because x-ray energy range for a crystal analyzer operating at high Bragg angles is typically limited to a narrow operating energy range, a large number of crystal analyzers are required for the spectrometer to operate over a sufficiently wide energy bandwidth; because a crystal analyzer operating at high Bragg angles typically reflects an energy bandwidth significantly narrower than the energy resolution required for XAS measurement, it leads to significant loss in measurement throughput. Additionally, XAS measurement is typically performed by scanning x-ray energy point by point.

There is therefore a need for a laboratory x-ray absorption spectroscopy system with high throughput that circumvents the limitations of prior laboratory XAS systems.

BRIEF SUMMARY OF THE INVENTION

Presented in this Application is a method and systems for performing x-ray absorption spectroscopy measurement and an x-ray absorption spectrometer to measure x-ray transmission with high throughput, high spatial, and high spectral resolution.
Apparatus The disclosed x-ray absorption spectrometer comprises a laboratory x-ray source, and an optical train which focuses x-rays over an energy bandwidth greater than 10 eV emerging from the x-ray source on or near an object to be examined with an focus size less than 500 micrometers. The benefits of the optical train include high x-ray flux on the sample and small illuminated spot for analyzing a small area (high spatial resolution) and use of crystal analyzers with low Bragg angles for high throughput, and compactness of the spectrometer. Additionally, it may also serves as a low-pass filter with a predetermined high-energy cut-off for the x-rays. The benefit of using an optical train that has properties enabling it to serve as low-pass focusing reflector is that the x-ray production efficiency of the x-ray source can be increased by enabling the energy of the bombarding electrons in the x-ray source to be substantially higher.

The x-ray optical elements in the train may comprise capillary x-ray optics, including reflecting surface profiles that correspond to one or more portions of quadric functions such as paraboloids, ellipsoids, or Wolter-type (e.g. paraboloidal and hyperboloidal profiles). Optical elements include but are not limited to x-ray mirror optics based on total external reflection. For an x-ray of incident at an angle $\vartheta$ onto a surface of a material with atomic number Z, the reflectivity is nearly 100% for near-grazing angles (e.g. $\vartheta \approx 0°$), and falls off for angles larger than a material-dependent and x-ray energy dependent critical angle $\vartheta_c$. Critical angles are typically smaller than 2°, limiting the acceptance angle for most x-ray optical systems.

In some cases where a narrow energy bandwidth is sufficient for XAS measurement, focusing multilayer optics such as Montel Optics may be used.

In some embodiments, the higher brightness compact x-ray source is achieved in part through the use of novel x-ray targets used in generating x-rays from electron beam bombardment. These x-ray target configurations may comprise a number of microstructures of one or more selected x-ray generating materials fabricated in close thermal contact with (such as embedded in or buried in) a substrate with high thermal conductivity, such that the heat is more efficiently removed from the x-ray generating material. This in turn allows bombardment of the x-ray generating material with higher electron density and/or higher energy electrons, which leads to greater x-ray brightness and greater x-ray flux.

An object to be examined is placed in the path of the focused x-ray beam, and an aperture may be placed at or near the point of focus to selectively pass the transmitted x-rays while restricting the widely radiated x-ray fluorescence. The object may be translated in the plane perpendicular with respect to the x-ray beam to allow 2-D "map" of the transmitted spectrum to be collected or rotated about its axis with or without translation so that 3D tomography of the transmission spectrum can be collected.

The x-ray absorption spectroscopy system comprises also at least one spatially resolved x-ray detector. The crystal analyzer is positioned to receive and diffract the x-rays transmitting through the object onto an spatially resolving detector, aligned so that different pixels of the detector correspond to different x-ray wavelengths.

DETAILED DESCRIPTIONS OF
EMBODIMENTS OF THE INVENTION

1. A Basic Embodiment of the Invention.

Figure 1:
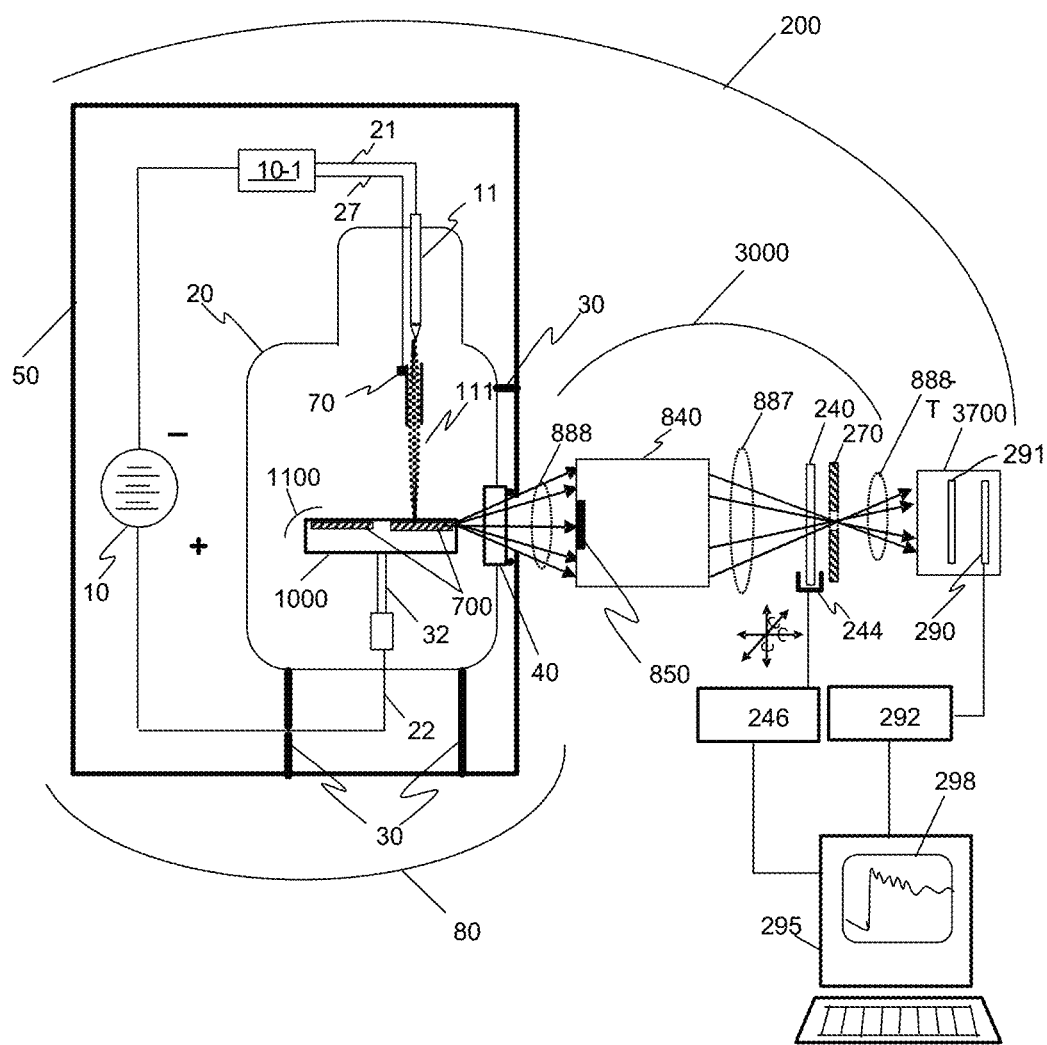
FIG. 1 illustrates a schematic cross-section view of elements of an embodiment of an x-ray spectrometer according to the invention.

FIG. 1 illustrates an embodiment of an x-ray spectrometer system 200 comprising an x-ray source 80, an x-ray optical system 3000 that includes an object 240 to be examined by x-ray transmission, also referred to as a sample by those skilled in the art, a spectrometer 3700 comprising a detector 290 and a crystal 291, and signal processing electronics 292 and an analysis system 295 with a display 298. The object 240 to be examined will also be referred to as the sample hereinafter.

The source 80 comprises a vacuum environment (typically $10^{-6}$ ton or better) commonly maintained by a sealed vacuum chamber 20 or active pumping, and manufactured with sealed electrical leads 21 and 22 that pass from the negative and positive terminals of a high voltage source 10 outside the tube to the various elements inside the vacuum chamber 20. The source 80 will typically comprise mounts 30 which secure the vacuum chamber 20 in a housing 50, and the housing 50 may additionally comprise shielding material, such as lead, to prevent x-rays from being radiated by the source 80 in unwanted directions.

Inside the vacuum chamber 20, an electron emitter 11 connected through the lead 21 to the negative terminal of a high voltage source 10, which serves as a cathode and generates a beam of electrons 111. Any number of prior art techniques for electron beam generation may be used for the embodiments of the invention disclosed herein, such as thermionic emission, field emission, Schottky emission, emitters comprising nanostructures such as carbon nanotubes), and by use of ferroelectric materials.

A target 1100 comprising a target substrate 1000 and one or more x-ray generating structure(s) 700 comprising one or more x-ray generating materials is electrically connected to the opposite high voltage lead 22 and target support 32 to be at ground or a positive voltage relative to the electron emitter 11, thus serving as an anode. The electrons 111 accelerate towards the target 1100 and collide with it at high energy, with the energy of the electrons determined by the magnitude of the accelerating voltage. The collision of the electrons 111 into the target 1100 induces several effects, including the radiation of x-rays 888, some of which exit the vacuum chamber 20 and are transmitted through a window 40 transmissive to x-rays.

In some instances of the invention, there may also be an electron control mechanism 70 such as an electrostatic lens system or other system of electron optics that is controlled and coordinated with the electron dose and voltage provided by the electron emitter 11 by a controller 10-1 through an additional lead 27. The electron beam 111 may therefore be scanned, focused, de-focused, or otherwise directed onto target 1100 comprising one or more x-ray generating structures 700 fabricated to be in close thermal contact with a substrate 1000.

Once the x-rays 888 exit the x-ray source 80, a portion of the x-rays are collected by optical system 3000, typically comprising one or more optical trains 840. In some embodiments, the optical trains comprise x-ray optical elements with axial symmetry such as capillary optics. The elements of the optical train 840 reflect x-rays at grazing angles to focus a portion 887 of the x-rays onto a focal spot. In many instances, an aperture component 270 having one or more apertures 272 is coincident with the focal spot. The object 240 to be examined is typically placed in a mount 244 and positioned just before the aperture 272. The mount may allow the object 240 to be translated and/or rotated so that different portions of the object 240 are illuminated by the converging x-rays 887, allowing different positions on the object 240 to be illuminated in a systematic scan or from several angles of incidence, with this motion controlled by a controller 246. X-rays propagating along the axis of the optical train that are not collected and focused may be blocked by a beam stop 850.

Once the focused portion of the x-rays 887 converge onto the object 240, the transmitted x-rays 888-T are collected by a spectrometer 3700. The spectrometer 3700 typically comprises at least one dispersing x-ray crystal 291 and an x-ray detector 290. In some instances, the distance between the apparent source of x-rays on the sample and the at least one analyzer crystal is less than two (2) meters. The detector 290 will typically be an array detector, positioned to record the intensity of the dispersed x-rays as a function of position. Additional signal processing electronics 292 and analysis system 295 correlate the intensity signals to the corresponding x-ray energy. The analysis system 295 may additionally comprise a display 298. The detector 290 may also comprise sensors and electronics that serve as an x-ray spectrometer, analyzing both the number of x-ray fluorescence photons emerging from the object 240 as well as their energy.

An x-ray optical train is placed downstream of the x-ray source to collect and focus a portion of the x-rays generated by the x-ray source. The x-ray optic has a cut-off energy above which x-ray reflection is reduced to 30% or less. The use of this optic enables the operation of the x-ray source at higher accelerating voltages that significantly increase efficient generation of bremsstrahlung radiation. In prior art, laboratory x-ray sources have been limited to operation of less than 2X the characteristic energy of interest of the element under examination, because of potential contamination from multiple order diffraction. In some instances, the x-ray optical train comprises at least one capillary x-ray optic with an inner surface profile that corresponds one or more portions of a quadric function, such as an ellipsoid, paraboloid, or a Wolter-type (paraboloid and ellipsoid/hyperboloid). In some instances, the x-ray optic may be a Montel mirror or other x-ray optics known to those versed in the art. In some instances, the optic may be coated with a coating such as a multilayer coating or a high atomic element (e.g. atomic number greater than 26) or alloy, such as Platinum.

The focal point of the x-ray optical train serves as a secondary source for a spectrometer comprising one or more crystals. Such spectrometers are described herein and comprise at least one x-ray crystal and one x-ray detector.

2. X-Ray Source Spectrum.

As was shown in FIG. 1, the x-ray source 80 will typically have a window 40. This window 40 may attenuate low energy x-rays. This window and/or the optical train may additionally comprise a filter, that such as a sheet or layer of aluminum, to further attenuate low energy x-rays.

If the optical train comprises one or more x-ray optical elements in which the x-rays illuminate the inner surface of the element at a near-grazing angle (e.g. at angles of a few degrees or smaller), the critical angle will be exceeded for the higher energy x-rays, and they will not be reflected. Thus, such optics have a "high-energy cutoff" for reflection. The "high-energy" cutoff is well defined for a given material and critical angle, and the attenuation of high energy x-rays prevents spurious signals coming from higher harmonics (e.g. twice (2×) the energy) from being observed downstream in the spectrometer. However, additional structure in the reflectivity spectrum may be observed at high energy with some materials. For some x-ray reflective optics, the reflectivity may be designed to be below 25% for all energies greater than 1.2 times the cutoff energy. For some x-ray reflective optics, the reflectivity may be designed to be below 10% for all energies greater than 1.2 times the cutoff energy.

3. Structured X-Ray Source.

Any number of x-ray sources known to those versed in the art may be used, such as commercial microfocus sources or rotating anode sources. In some preferred embodiments, x-ray sources comprising targets of multiple "wires" of x-ray materials in close thermal contact with a thermally conductive substrate are used. This may be achieved by any number of methods known in the art, such as sputtering or by brazing multiple materials upon a substrate. The electron beam and target may be moved relative to each other such that different target materials are bombarded and produce different spectra. In some embodiments, the x-ray generating materials are microstructured.

Additional embodiments of x-ray sources have been described in the U.S. Patent Applications X-RAY SOURCES USING LINEAR ACCUMULATION (U.S. patent application Ser. No. 14/490,672, filed Sep. 19, 2014 and now issued as U.S. Pat. No. 9,390,881), X-RAY SOURCES USING LINEAR ACCUMULATION (U.S. patent application Ser. No. 14/999,147, filed Apr. 1, 2016, and now issued as U.S. Pat. No. 9,543,109), and DIVERGING X-RAY SOURCES USING LINEAR ACCUMULATION (U.S. patent application Ser. No. 15/166,274 filed May 27, 2016), all of which are hereby incorporated by reference in their entirety, along with any provisional Applications to which these Patents and co-pending Patent Applications claim benefit.

Any of the target and/or source designs and configurations disclosed in the above referenced Patents and Patent Applications may be considered for use as a component in any or all of the methods or systems disclosed herein. Such variations may include active cooling systems comprising channels that carry liquid near or into the target to remove heat. It should be noted that these illustrations are presented to aid in the understanding of the present technology, and the various elements (microstructures, surface layers, cooling channels, etc.) are not drawn to scale in these figures.

It should also be noted that the x-ray source used for various embodiments of the present technology may, as described, be a microfocus source using bombardment of a solid anode target by electrons or a target comprised of a metal layer deposited on a substrate. The target may also comprise multiple x-ray generating materials, such as stripes of sputtered materials or wires brazed on a substrate, and/or may additionally contain regions in which the x-ray generating materials are molten or liquid. Furthermore, the x-ray source may be any one of a number of other x-ray sources designed to use a liquid metal (such as a gallium liquid metal jet) as the anode. The x-ray source target material(s) is preferably selected to optimize the generation of x-rays at energies slightly above the absorption edge of a predetermined element of interest.

Figure 2:
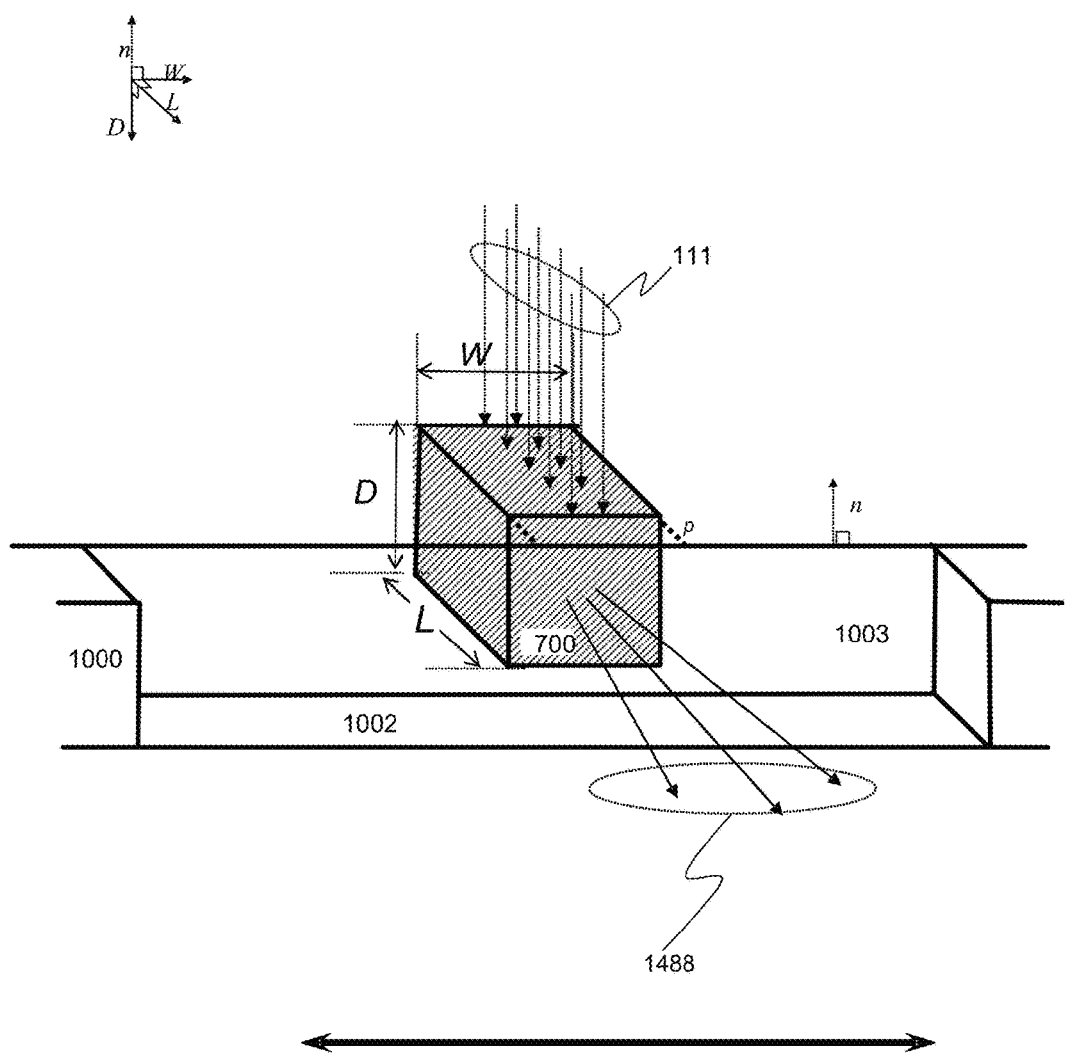
FIG. 2 illustrates a portion of a target comprising a single block of x-ray generating material as may be used in some embodiments of the invention. As drawn, the x-rays 1488 emerge at a zero take-off angle relative to the surface, but other alignments using a non-zero-degree take-off angle may be used as well.

An illustration of a portion of a target as may be used in some embodiments of the invention is presented in FIG. 2, in which an x-ray generating region comprising a single microstructure 700 is configured to be embedded into a substrate 1000 at or near a recessed edge 1003 of an optional recessed shelf 1002 near an edge of the substrate 1000. The x-ray generating microstructure 700 can be in the shape of a rectangular bar of width W, length L, and depth or thickness D that is embedded in the substrate 1000 and generates x-rays 1488 when bombarded with electrons 111. The thickness of the bar D (along the surface normal of the target) is selected to be between one third and two thirds of the electron penetration depth of the x-ray generating material at the incident electron energy. The x-ray generating material used in the target should ideally have good thermal properties. The x-ray generating material should additionally be selected for good x-ray production properties, which includes x-ray production efficiency (proportional to its atomic number) and in some cases, it may be desirable to produce a specific spectra of interest. The material of the substrate 1000 may also be chosen to have a high thermal conductivity, typically larger than 100 W/(m °C.) at room temperature.

Figure 3:
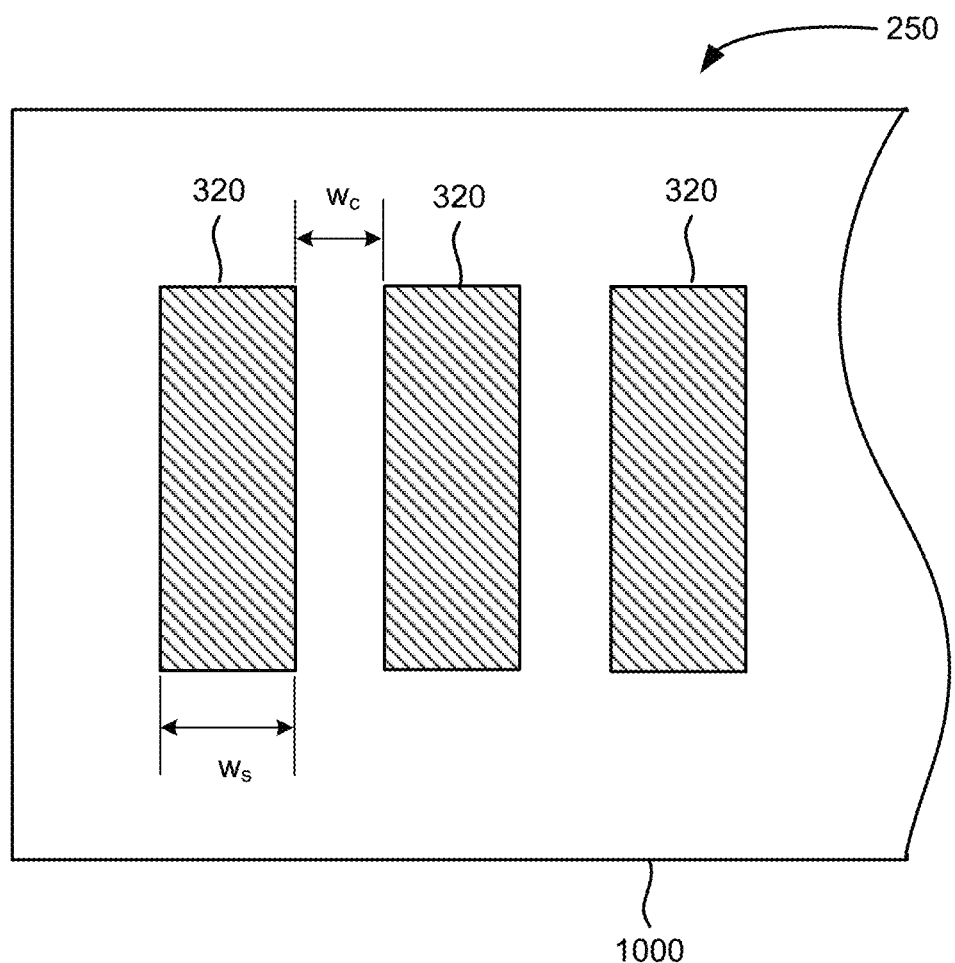
FIG. 3 illustrates a top view of a target having multiple wire microstructures.

In some instances, the substrate may include one or high aspect ratio ("wire") microstructures. FIG. 3 illustrates a top view of a target having multiple wire microstructures. Target 250 includes wire microstructures 320 and substrate 310. Spacing between the microstructures 320 may be lower bound to avoid creation of x-rays from an adjacent target when an electron-beam strikes a single target microstructure. Microstructures 320 may be any of a plurality of metals or alloys, such as Ti, Al, Cu, Cr, Fe, Mo, Rh, Co, W, Pt, Ag, and Au, and each microstructure can be a different material from other microstructures, allowing each wire 320 to generate x-rays with different spectra. In some instances, multiple wires of the same material can be implemented in the present system, to provide a longer use or lifetime of the system. Substrate 310 may be any highly thermal conductive material, such as for example diamond or copper.

The width of the space between microstructures $W_C$ can be 15 μm (microns) or more. The width of a wire microstructure Ws can be less than or equal to 250 or 300 μm (microns). The substrate can extend longer than one or more microstructures, as shown in FIG. 3, or may have the same length and be flush with one or more microstructures. In some instances, the wire microstructures 320 can be embedded within the substrate 1000. The embedded wires can have a cross section that is rectangular (as illustrated in FIG. 32), curved, circular, square, or any other shape. In some instances, the target can have multiple surface mounted wire microstructures.

In some embodiments but not shown in FIGS. 32 and 33, there may be one or more layer(s) 422 between the microstructures and substrate. These may contain a material that prevents diffusion (e.g. Ta) and/or a material that improves the thermal conductance between the microstructures and substrate (e.g. Cr between Cu and diamond).

X-ray generating structures with at least one dimension smaller than 1 mm, or even as small as nano-scale dimensions (i.e. greater than 10 nm) may also be described by the word "microstructures" as used herein as long as the properties are consistent with the geometric factors for sub-source size and grating pitches set forth in the various embodiments. Some microstructures may have one dimension (e.g. L) being several millimeters or in excess of 1 cm, with the other dimensions being sub-250 um for example.

The electron beam is directed onto different target materials either by moving the anode or by directing the electron beam by the use of electron control mechanism(s). The x-ray source window is aligned such that the take-off angle of the x-rays are at fewer than 30 degrees.

An alternative approach may be found in distributing the x-ray generating material within the substrate. An illustration of a portion of an alternative target as may be used in such embodiments of the present technology is presented in FIG. 4. In this target, an x-ray generating region 710 with microstructures 711-717 is configured at or near a recessed edge 1003 of the target substrate 1000 on a shelf 1002 and generate x-rays 1788 when bombarded with electrons 111.

The bars may be embedded in the substrate (as shown) or on top of the substrate.

Other target configurations that may be used in embodiments of the invention, as has been described in the above cited U.S. patent application Ser. No. 14/465,816, are microstructures comprising multiple x-ray generating materials, microstructures comprising alloys of x-ray generating materials, microstructures deposited with an anti-diffusion layer or an adhesion layer, microstructures with a thermally conducting overcoat, microstructures with a thermally conducting and electrically conducting overcoat, microstructures buried within a substrate and the like.

Figure 4:
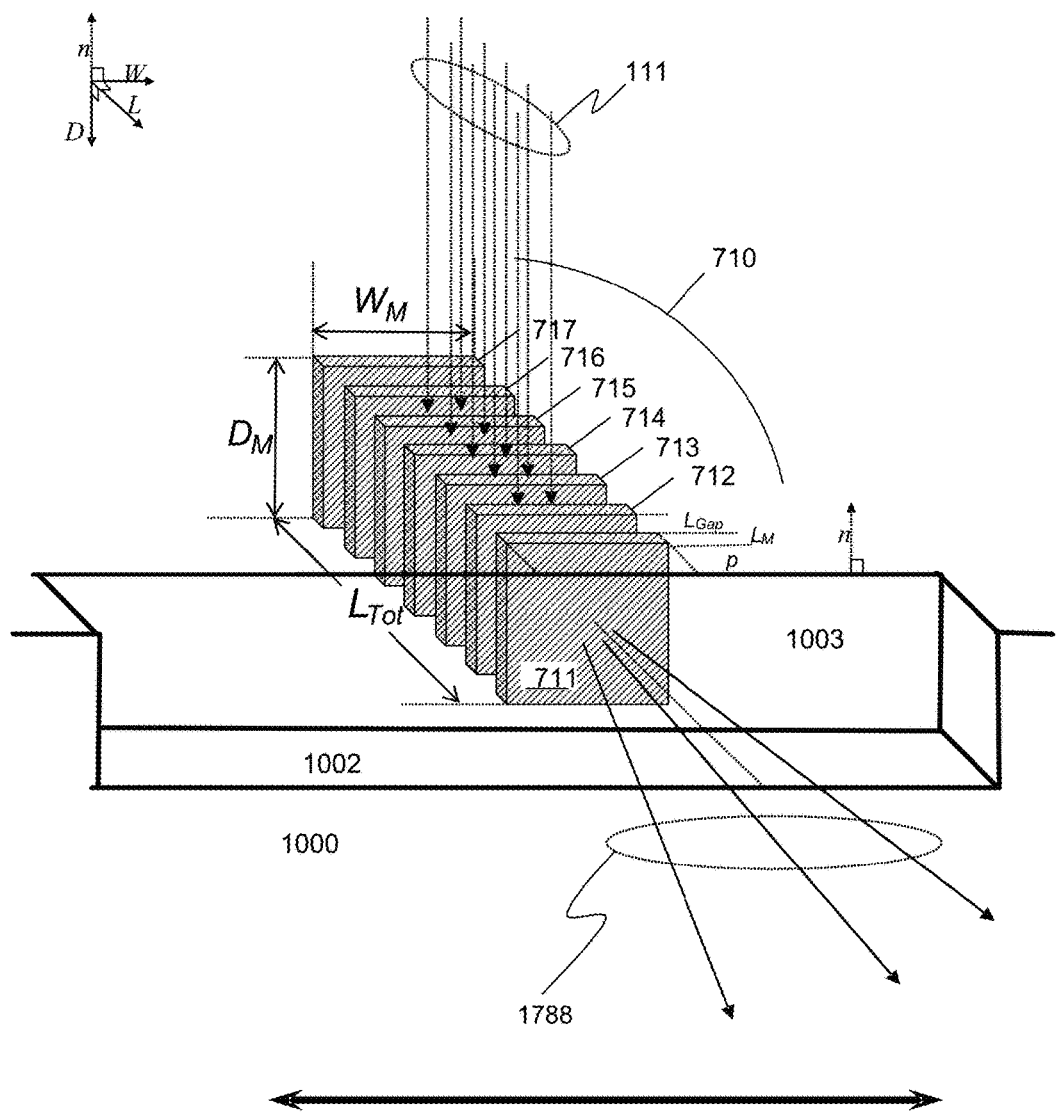
FIG. 4 illustrates a portion of a target comprising a several microstructures of x-ray generating material as may be used in some embodiments of the invention.
Figure 5A:
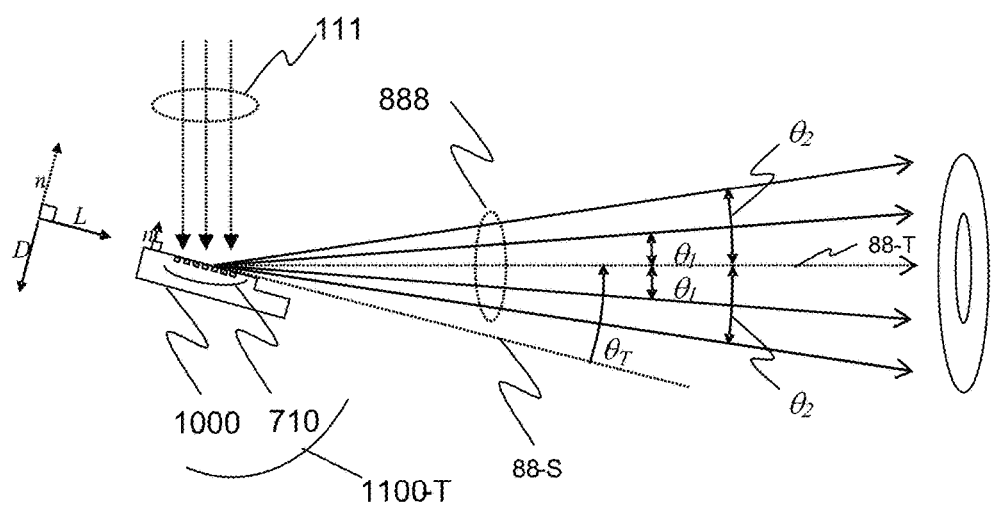
FIG. 5A illustrates a cross-section schematic view of an x-ray target generating x-rays as may be used in some embodiments of the invention.
Figure 5B:
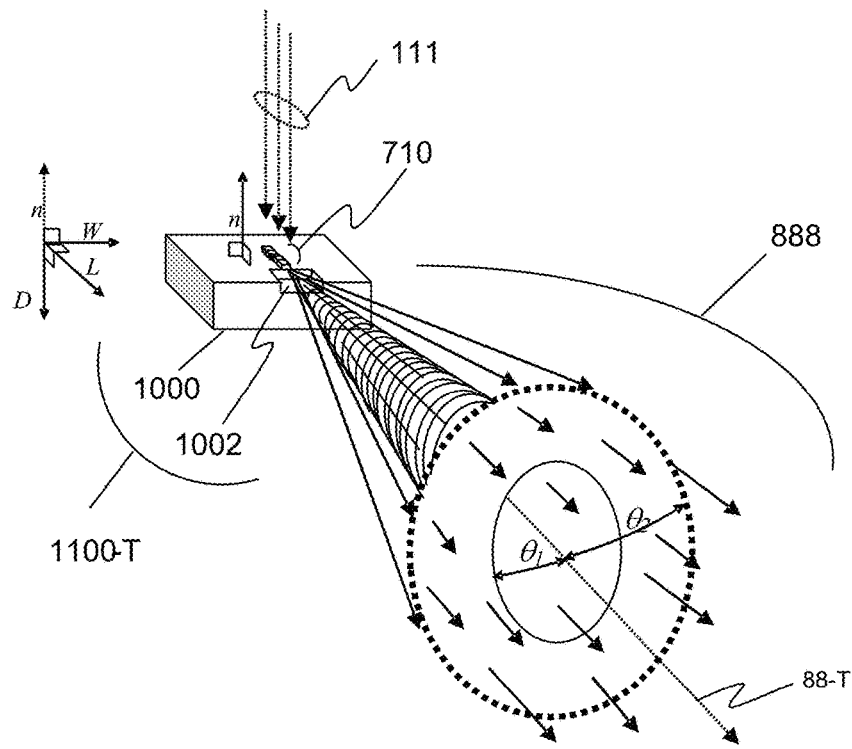
FIG. 5B illustrates a perspective schematic view of the x-ray target and x-ray radiation of FIG. 5A.
Figure 5C:
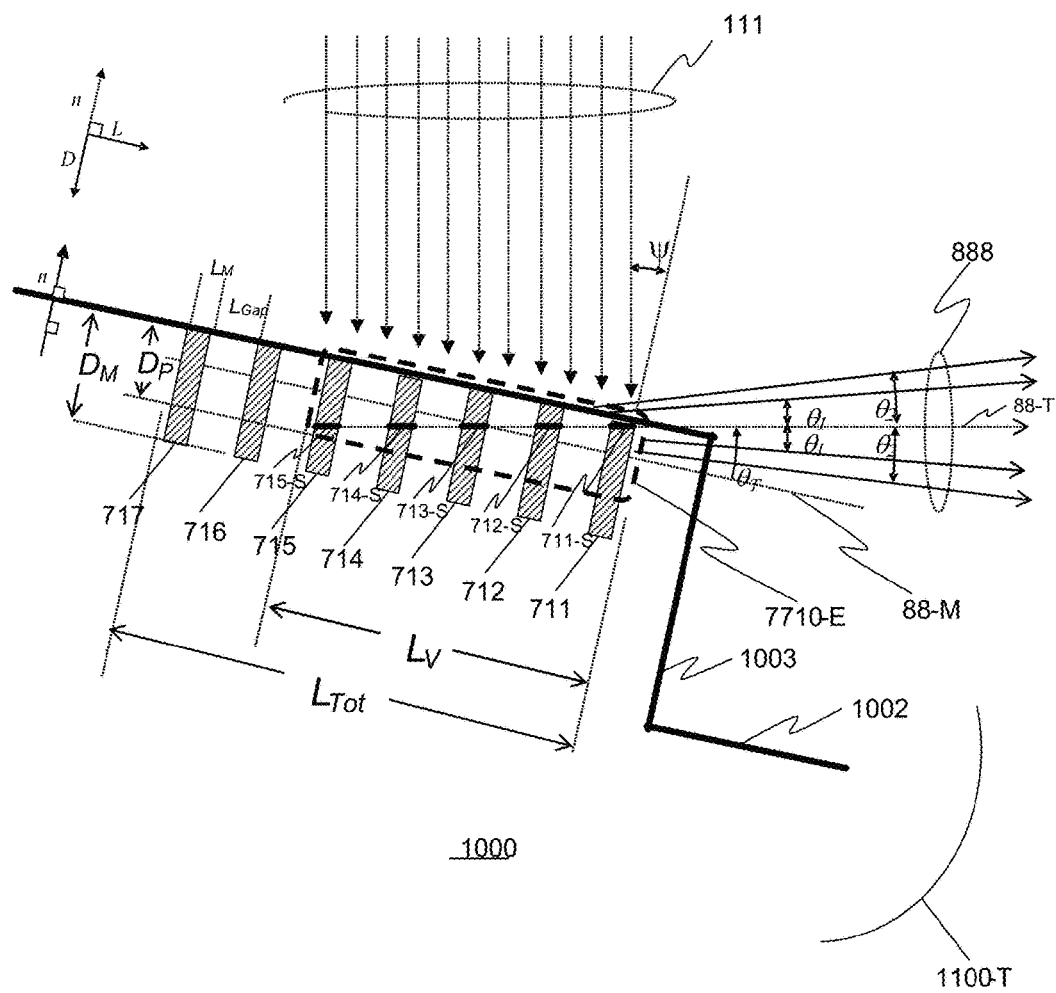
FIG. 5C illustrates more detailed cross-section schematic view of the x-ray target and x-ray radiation of FIG. 5A.

FIGS. 5A-5C illustrate an example of a target 1100-T comprising a set 710 of microstructures of x-ray generating material 711, 712 . . . 717 embedded within a substrate 1000, similar to the target shown in FIG. 4. When bombarded by electrons 111 within a vacuum chamber, the x-ray generating material produces x-rays 888.

For the target as illustrated, there is furthermore a predetermined take-off direction (designated by ray 88-T) for the downstream formation of an x-ray beam. This take-off direction is oriented at an angle $\theta_T$ relative to the local surface.

As illustrated in FIGS. 5A-5C, a predetermined set of cone angles is defined, centered around the take-off angle $\theta_T$. A ray propagating along the innermost portion of the cone makes an angle $\theta_1$ with respect to the take off angle, while a ray propagating along the outermost portion of the cone makes an angle $\theta_2$ with respect to the take off angle. These cone angles are generally quite small (less than 50 mrad), and the take-off angle is generally between 0° to 6° (0 to 105 mrad), although in some circumstances a take off angle as large as 11.5° (~200 mrad) may be used.

Figure 6:
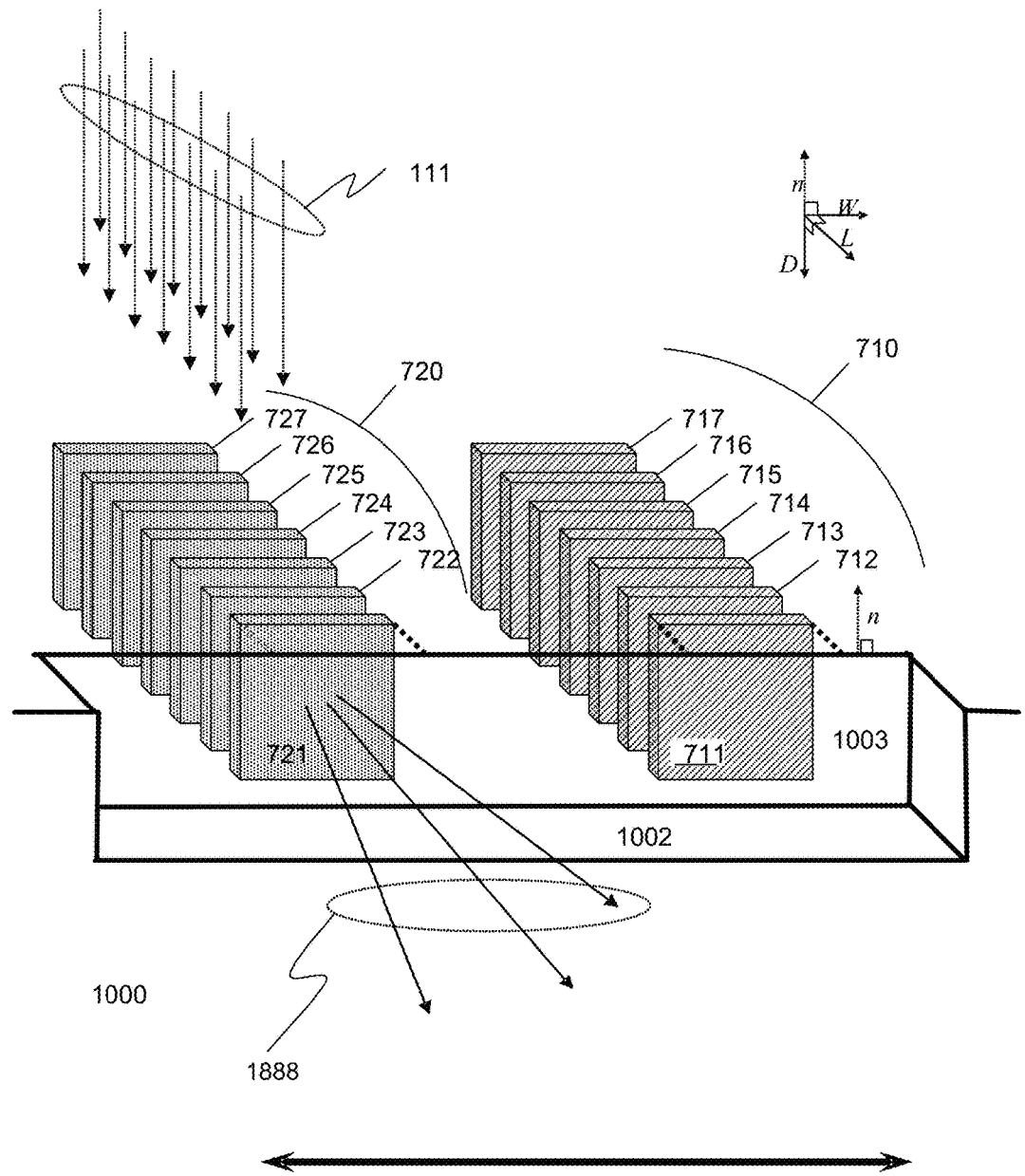
FIG. 6 illustrates a portion of a target comprising two groups of microstructures, each having a different x-ray generating material, as may be used in some embodiments of the invention.

FIG. 6 represents a portion of a target having two sets of microstructures of x-ray generating materials as may be used in an alternative implementation. In this instance, one set of microstructures 710, as before, comprises seven microstructures 711-717 of any material selected for the spectral x-ray radiation properties.

However, the target of FIG. 6 also comprises a second set of microstructures 720, also comprising seven microstructures 721-727 of a second predetermined x-ray generating material, which is distinct from the first x-ray generating material. By translating the target or by moving the electron beam so that the electrons 111 now bombard the second set of microstructures, a second set of x-rays 1888 are produced. As drawn, the x-rays 1888 emerge at a zero degree take-off angle relative to the surface but any non-zero take-off angle may be used. If the materials of the first set 710 and second set 720 are distinct, the corresponding x-rays 1788 and 1888 generated when selected for bombardment by electrons will also have distinct spectral properties.

Figure 7:
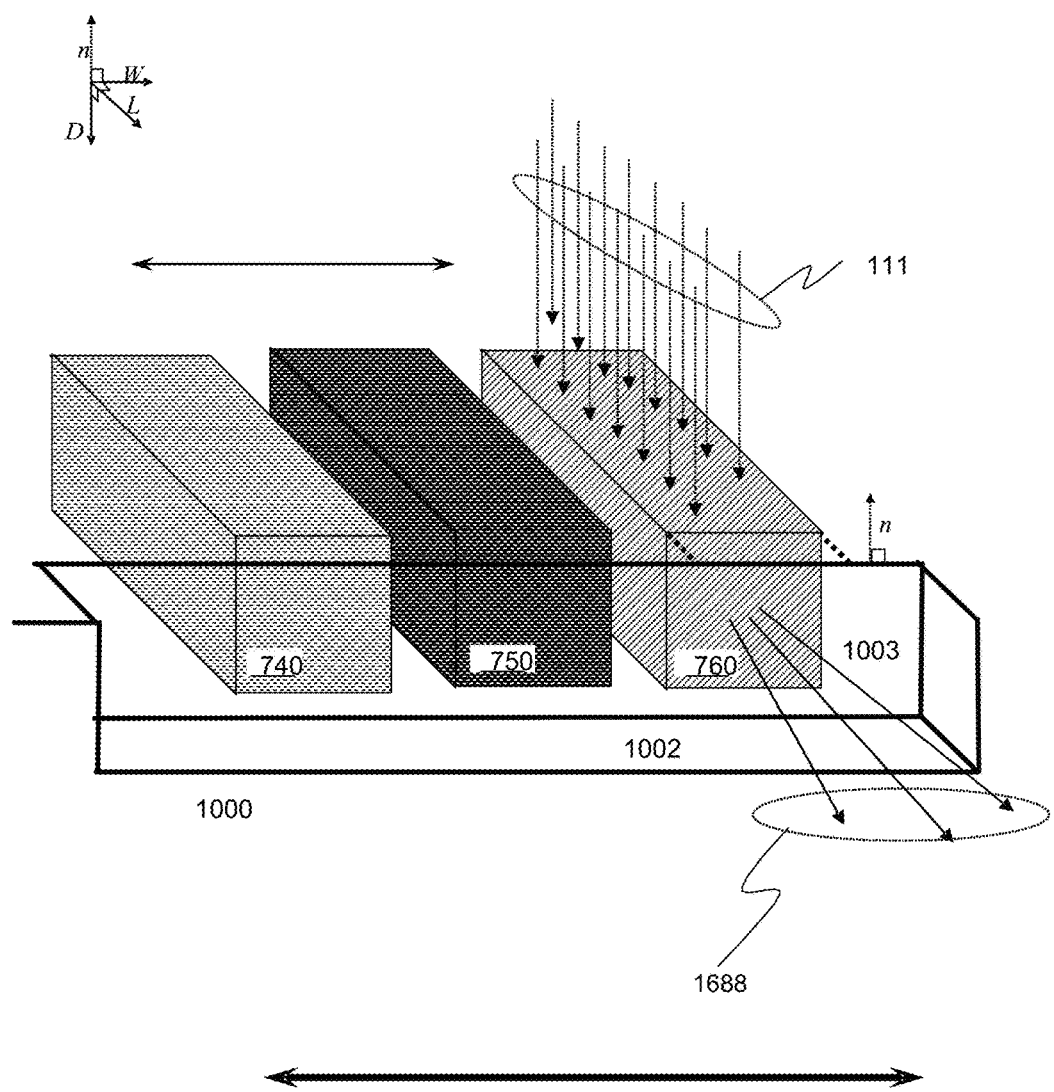
FIG. 7 illustrates a portion of a target comprising three x-ray generating structures, each having a different x-ray generating material, as may be used in some embodiments of the invention.

As illustrated in FIG. 7, multiple solid structures 740, 750 and 760 of different x-ray generating materials may be used in an anode target as well.

Although the physical translation of the target under the electron beam may allow the materials to be "switched" from one to another while producing a beam that remains aligned with a single set of x-ray optics, other embodiments in which the electron beam is simply directed from one set of materials to another may also be used. This may be beneficial in cases where the different x-ray generating materials are aligned with different sets of x-ray optics, with each set of optics tuned to match the radiation spectrum of x-rays for each material. A target material and optical system may be considered "matched" when the cutoff energy of the optical system is above a strong characteristic line of the target material and when the optical system is designed to optimize reflection of the selected characteristic line.

4. X-Ray Optical System.

Once x-rays are generated by a high-brightness x-ray source, a portion of the x-rays can be collected by an optical train to be subsequently collimated and/or focused onto the object to measure the x-ray absorption and transmission. In many instances, this optical system will comprise x-ray reflectors that collect and focus x-ray energies of a bandwidth greater than 0.1% of an x-ray energy of interest.

Optical trains such as may be used in embodiments of the invention disclosed herein have been described in detail in the US Patent Application entitled X-RAY ILLUMINATORS WITH HIGH FLUX AND HIGH FLUX DENSITY (U.S. patent application Ser. No. 15/431,786, filed Feb. 14, 2017) and its parent Applications (U.S. patent application Ser. No. 15/269,855, filed Sep. 16, 2016, and now issued as U.S. Pat. No. 9,570,265, and Ser. No. 14/544,191, filed Dec. 5, 2014 and now issued as U.S. Pat. No. 9,449,781), which are all hereby incorporated by reference in its entirety, along with the provisional Applications to which they claim benefit.

Referring back to the general illustration of FIG. 1, in general, the generated x-rays will diverge from the x-ray source 80, and an optical train 3000 comprising a set of one or more x-ray optical elements will collect a portion of the x-rays and redirect their path of propagation.

The optical train 3000 may be a simple, single x-ray reflecting optical element with the topology of a hollow tube (e.g. capillary tube), or a more complex set of x-ray optics. This optical train 3000 can be aligned along the axis of brightest illumination so that a portion of the diverging x-rays 888 will reflect off the inner surface. The curvature of the inner surface may take a number of geometric forms, but a very useful set of geometric forms for a number of optical elements are found among the quadric surfaces. Examples of reflecting surface profiles corresponding to one or more portions of ellipsoids, paraboloids, hyperboloids, elliptic cylinders, cylinders, and conical (or 2D versions of the 3D shapes mentioned above).

For the embodiments presented here, the optical train produces a focused beam of x-rays. In some embodiments, an optional aperture 272 may be placed in the same plane as the focal plane to reduce background from scattered x-rays which helps to improve the signal-to-background ratio of the system. By placing an object 240 to be examined where it will be illuminated by the converging x-rays 887, a transmitted diverging x-ray wavefront 888-T is produced on the far side of the focal plane and may be subsequently analyzed by the spectrometer.

Note that these the following figures illustrating various optical trains are not drawn to scale, but drawn to illustrate the operating principle more clearly.

4.1. Ellipsoidal Optics.

Figure 8A:
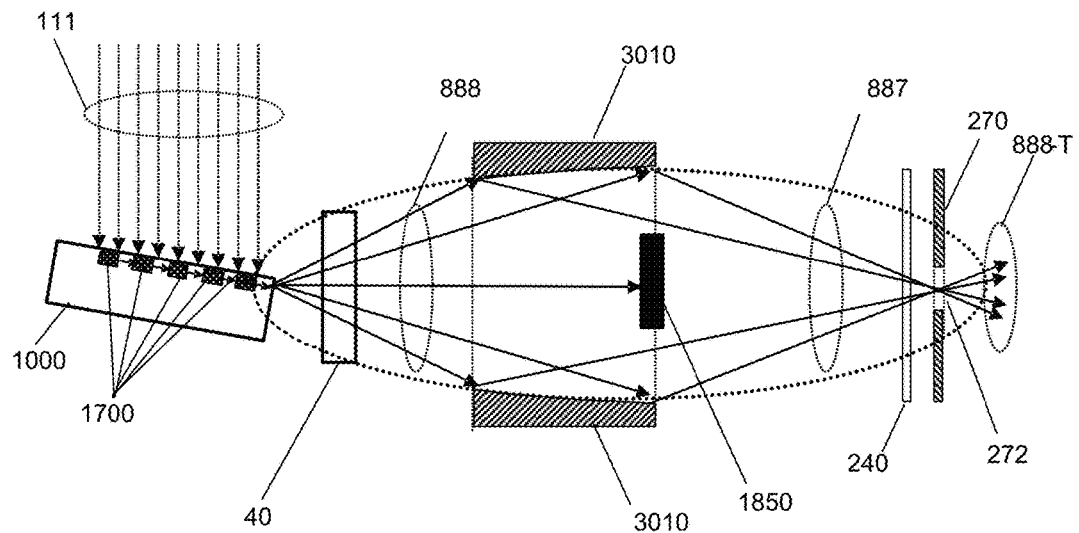
FIG. 8A illustrates a cross section schematic view of an x-ray source and an optical train comprising an ellipsoidal optical element as may be used in some embodiments of the invention.

FIG. 8A illustrates in cross section a possible optical configuration for the optical train using the form of an ellipse. An elliptical capillary optic has two foci $F_1$ and $F_2$ such that any photons radiating from one of the foci will be reflected and converge onto the other.

Figure 8B:
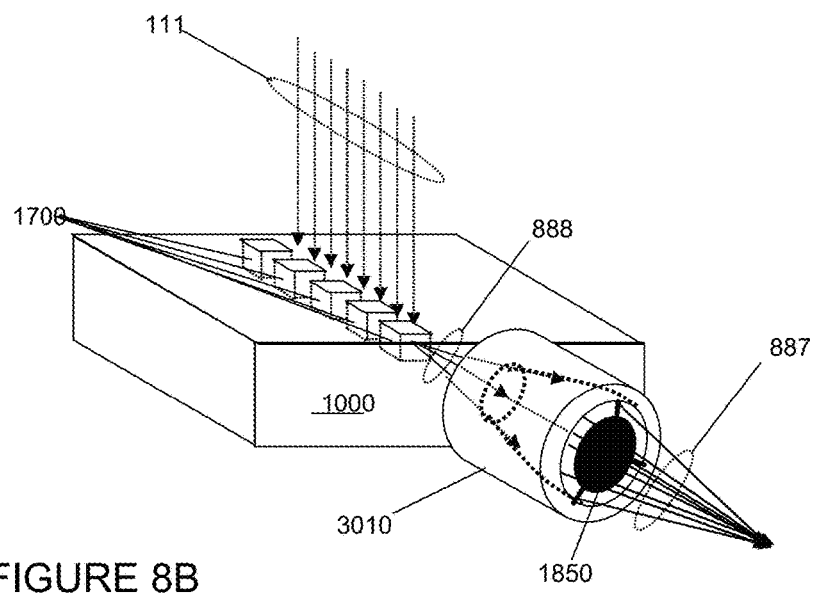
FIG. 8B illustrates a perspective schematic view of a portion of an x-ray source and optical train.

FIGS. 8A-8B illustrate a portion of an embodiment of the invention utilizing such an ellipsoidal reflector 3010. An x-ray source generates diverging x-rays 888 that enter the ellipsoidal optical element 3010. A portion of the x-rays experience total external reflection from the inner elliptical surface of a tube-like optical element 3010, and become focused x-rays 887 that pass through an object 250 to be examined and arrive at a focal point. An aperture 272 in aperture component 270 is placed coincident with the focal plane.

FIG. 8A illustrates x-rays 888 generated by bombarding microstructures 1700 with electron beam 111. Though x-rays 888 are illustrated as emitting from a single point on microstructure 1700, the x-rays may be generated by different and/or all portions of a microstructure. The emission of x-rays from a single point in FIG. 8A and other figures is illustrated for purposes of simplicity and not intended to be limiting. In some embodiments, as illustrated in FIG. 8A and the corresponding perspective view of FIG. 8B, the on-axis x-rays may be blocked with a beam stop 1850. In some instances, beam stop 1850 of the system of FIG. 8A, and in other systems and configurations disclosed herein, may be positioned on the incident beam side of the optical element 3010 or other locations (e.g. exit).

The optic element of the system described herein may include one or more reflectors that are matched to one or more target materials. The matching may be achieved by selecting optics with the geometric shape, size, and surface coating that collects as many x-rays as possible from the source and at an angle that satisfies the critical reflection angle of the x-ray energies of interest from the target. In some instances, the matching is based on maximizing the numerical aperture (NA) of the optics for x-ray energies of interest. The optic elements may be configured to focus or collimate the beam.

It should be noted that the drawings presented here are not illustrated to scale, but have been created to better point out how the invention is to be made and used.

4.2. Paraboloidal Optics.

In some instances, another possible optical configuration for the optical train uses the form of two parabolas. A parabola can have a single focus $F_p$ such that any photons radiated from the point of focus will be reflected to form a parallel (collimated) beam.

Figure 9A:
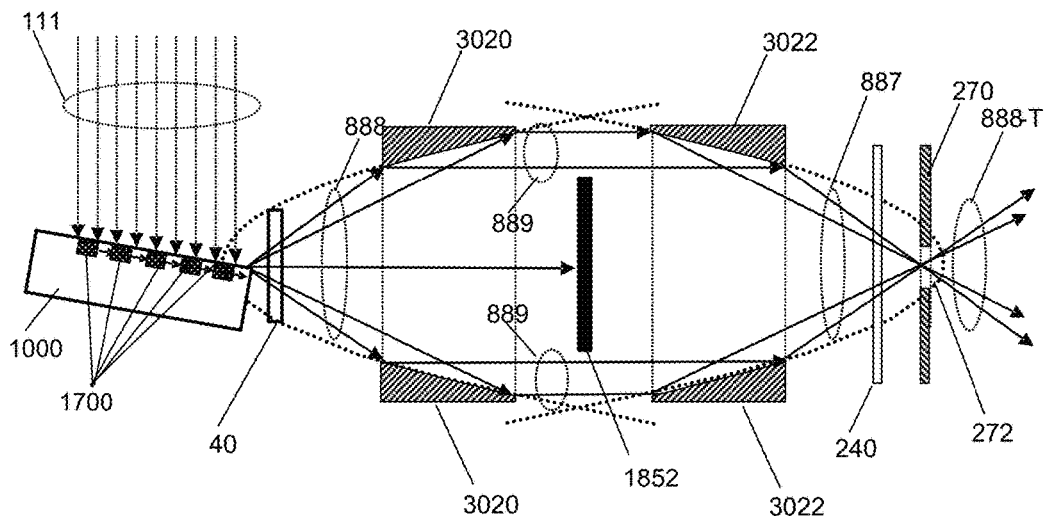
FIG. 9A illustrates a cross section schematic view of an x-ray source and an optical train comprising a pair of paraboloidal optical elements.
Figure 9B:
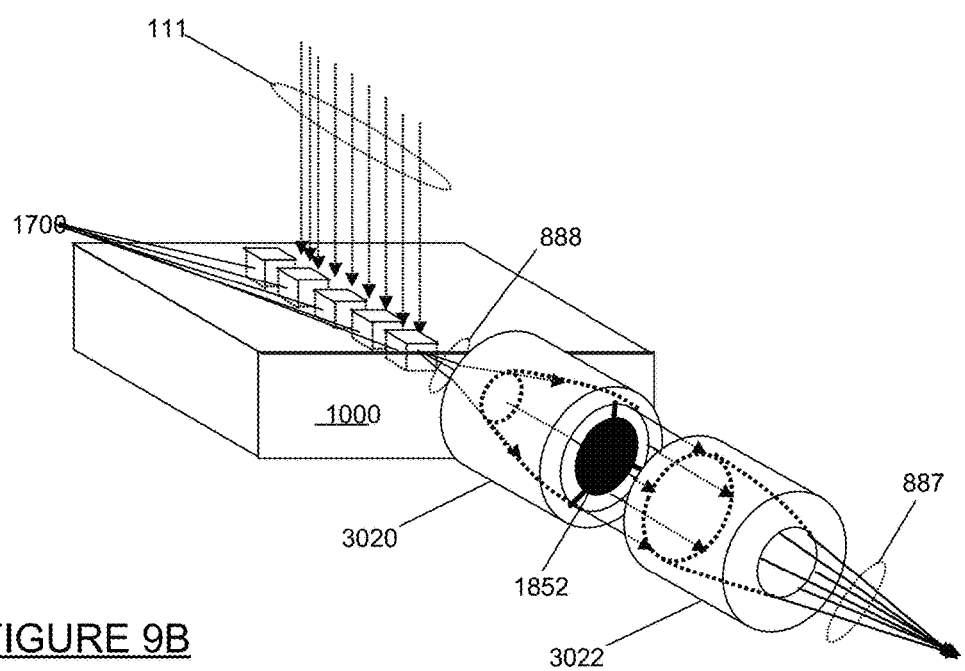
FIG. 9B illustrates a perspective schematic view of a portion of an x-ray source and optical train.

FIG. 9A-9B illustrates a portion of an embodiment of the invention utilizing a paraboloidal reflector 3020. Electron beams 111 bombard a target 1000, which is at a near zero angle (as shown), to provide an x-ray source or at a shallow angle such as 6 degrees. The x-ray source generates diverging x-rays 888 that enter a first paraboloidal optical element 3020. A portion of the x-rays experience total external reflection from the inner paraboloidal surface of the tube-like optical element 3020, and become collimated x-rays 889.

Once collimated, a second optical element 3022 with a tube-shaped topology and paraboloidal inner surface, as shown in FIGS. 9A and 9B, may be aligned with the optical axis of the first optical element 3020 so that the collimated x-rays 889 are incident on the inner surface of the second optical element 3022 at angles smaller than the critical angle for the surface. In some embodiments, this second optical element is not a separate component but instead a different profile prescription than the first optical element and contained within the same capillary. The reflected x-rays then become focused x-rays 887 that converge onto a focal point after passing through an object 240 to be examined. An optional aperture 272 is placed at the focal plane of the second optical element.

Although the illustration shows a second paraboloidal optical element 3022 of the same size and shape as the initial paraboloidal optical element 3020, these need not be the same dimensions and may have different curvature and relative focus positions.

In some embodiments, as illustrated in FIG. 9A and the corresponding perspective view of FIG. 9B, the on-axis x-rays may be blocked with a beam stop 1852. Although shown positioned between the two paraboloidal optical elements, the beam stop may be positioned at different positions with respect to the optic, including at the entrance to the first optical element 3020 or at the exit of the second optical element 3022 as well.

4.3. Other X-Ray Optics.

Other x-ray optical systems, such as Wolter Type I optics, cone shaped capillary optics, polycapillary optics, Kirkpatrick-Baez optics, Montel mirrors, etc. may be used as components of the optical train. Systems comprising filters and additional beam stops, etc. may also be used.

The optical elements described above may be fabricated of any number of optical materials, including glass, silica, quartz, BK7, silicon (Si), Ultra-low expansion glass (ULE™), Zerodur™ or other elemental materials.

The reflective coatings used for the various optical elements used in embodiments of the invention as described above may be a single elemental material, to take advantage of the total external reflection for angles of incidence smaller than the critical angle, and preferably may be coated with a layer of higher mass density material (greater than 2.5 g/cm$^3$) at least 25 nm thick. Materials such as gold (Au), silver (Ag), platinum (Pt), etc. may be used as single-material coatings for these optical elements.

The reflective coatings may also be multilayer coatings, with alternating periodic layers of two or more materials, that provide constructive interference in reflection for certain x-ray wavelengths. The reflection efficiency depends on the wavelength and angle of incidence of the x-rays as well as the thickness of the alternating layers, so this has limited use as a broad band reflector, but may be used if a narrow energy band is desired. Combinations that may be used for multilayer reflectors are tungsten/carbon (W/C), tungsten/silicon (W/Si), tungsten/tungsten silicide (W/WSi$_2$), molybdenum/silicon (Mo/Si), nickel/carbon (Ni/C), chromium/scandium (Cr/Sc), lanthanum/boron carbide (La/B$_4$C), tungsten/boron carbide (W/B$_4$C), and tantalum/silicon (Ta/Si), among others. The surface may also be a compound coating comprising an alloy or mixture of several materials.

Other x-ray optical elements, such as Fresnel Zone Plates, cylindrical Wolter optics, Wolter Type II or III optics, Schwarzschild optics, diffraction gratings, crystal mirrors using Bragg diffraction, hole-array lenses, multi-prism or "alligator" lenses, rolled x-ray prism lenses, "lobster eye" optics, micro channel plate optics may be used or combined with those already described to form compound optical systems for embodiments of the invention that direct x-rays in specific ways that will be known to those skilled in the art.

5. Spectrometer and Detector.
5.1. Basic Spectrometer.

Figure 10:
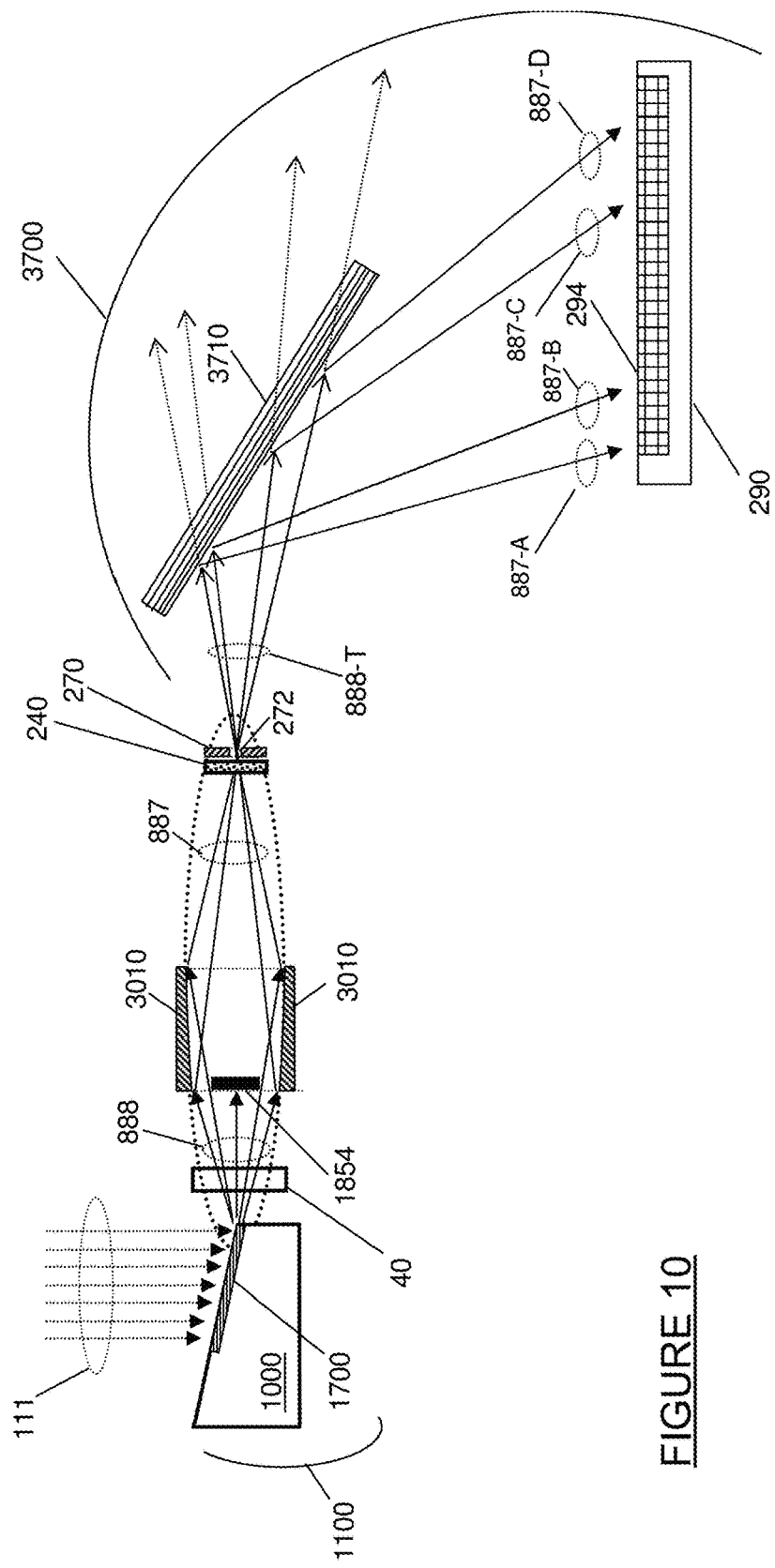
FIG. 10 illustrates a cross section schematic view of a spectrometer system using a single analyzer crystal.
Figure 11:
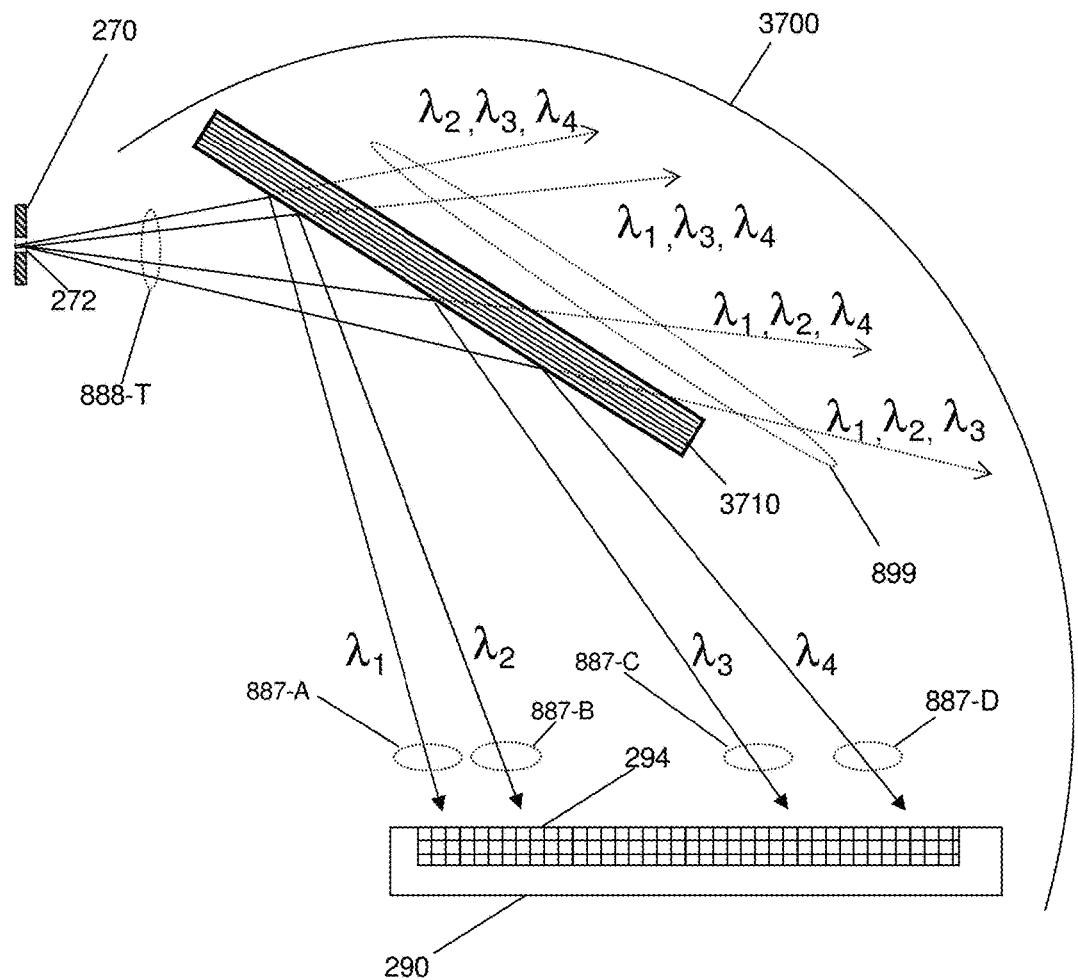
FIG. 11 illustrates a cross section schematic view of a spectrometer portion.
Figure 12:
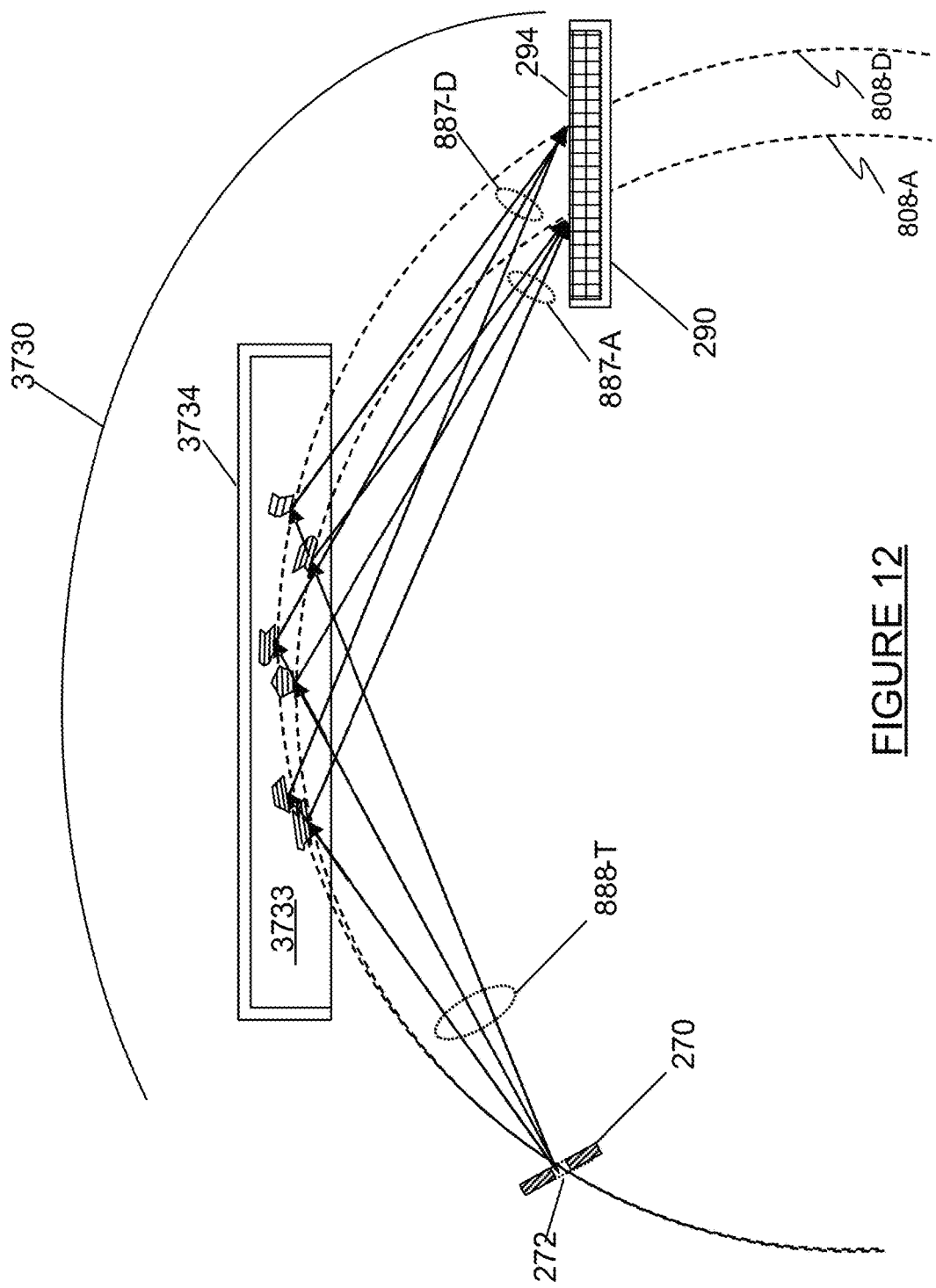
FIG. 12 illustrates a schematic view of a spectrometer arranged to show related Rowland Circles.

FIGS. 10-12 illustrate schematic cross-section views and a perspective view the elements of a spectrometer system that may be used in some embodiments of the invention. In FIG. 10, the x-ray target 1100 comprising a substrate 1000 and x-ray generating material 1700 is bombarded by electrons 111 in a vacuum. As drawn, the x-rays 888 emerge at a non-zero take-off angle relative to the surface.

The x-rays 888 that diverge from the x-ray source pass through the window 40 in the vacuum chamber and are collected by an optical train. In the example of FIGS. 10-12, the optical train comprises a single capillary optic 3010 and a beam stop 1854. This single optic 3010 has an inner ellipsoidal surface that reflects x-rays at near-grazing angles and focuses them onto a focal point. An optional aperture 272 with an aperture component 270 is coincident at the focal point. An object 240 to be examined is positioned before the aperture component 270, and the x-rays passing through the aperture 272 are those that have been transmitted through the object 240.

The aperture 272 will typically be a small hole of a diameter comparable to the size of the focused spot produced by the x-ray optical train. Aperture diameters of 5 to 25 microns may be typical in some embodiments of the invention. In some embodiments of the invention, the aperture may comprise a slit, generally oriented horizontally (i.e. in the direction parallel to the sagittal plane). The aperture component itself may comprise a piece of metal (e.g. molybdenum or platinum) having a thickness shorter than the depth of focus for the optical system (e.g. on the order of 20 microns thick).

On the far side of the aperture component 270, the x-rays emerge from the point of focus as diverging x-rays 888-T. The geometry will generally be an annulus of x-rays, as defined by the focusing lens 3010. As shown, the aperture 272 serves as the point of origin for the x-rays entering the spectrometer 3700. Additional apertures may also be used within the spectrometer, such as in front of the detector.

In some embodiments of the spectrometer, it is a parallel detection spectrometer as known in the art [see "D B Wittry, 'X-ray crystal spectrometers and monochromators in microanalysis.' *Microsc. Microanal.* 7, 124-141 2001"]. In such spectrometers, the diverging annular cone of x-rays 888-T will fall onto the surface of a diffracting analyzer crystal 3710, which will diffract x-rays of different wavelengths $\lambda_1$, $\lambda_2$, $\lambda_3$ $\lambda_4$, etc. (shown as ray bundles 887-A, 887-B, 887-C, and 887-D etc., respectively) to different points on positionally sensitive detector 290 with a sensor sensor 294. As shown in FIG. 10 and, in more detail in FIG. 11, the crystal analyzer will act as a Bragg diffraction element. X-rays that are not diffracted 899 are typically transmitted through the crystal analyzer and may be absorbed by a beam stop (not shown).

The crystal analyzer 3700 may be positioned ~250 mm away from the aperture 272 and will typically have a width of about 2 cm. and a length of about 5 cm, but other dimensions may be used. The crystal analyzer 3700 may comprise a single planar Bragg crystal, but in practice, the analyzer crystal may also comprise a thin crystal curved in the sagittal direction. This allows the x-rays diverging in the directions perpendicular to the direction of propagation to be collected and focused onto the detector 290, while allowing the x-rays to be diffracted by wavelength along the direction of propagation. Such orientations are sometimes called a von Hamos Spectrometer. In some implementations, the crystal may be doubly curved. For some implementations, a bending radius between 50 and 200 mm may be used. In other implementations, parallel detection spectrometers may be of geometries and designs that have been proposed by Schnopper, Birks, Henke, Zaluzec, Fiori, and others.

Curved crystal analyzers such as those made from thin wafers of single crystal silicon (e.g. aligned with the surface along the 111 or the 220 planes) may be used in some embodiments of the invention. Single crystal silicon analyzers may be grown onto a curved substrate, or thinned from previously grown silicon wafers and bent.

Crystal analyzers comprising graphite may also be used, in particular those comprising graphite layers aligned along the 002 plane such as highly oriented pyrolytic graphite (HOPG), or highly annealed pyrolytic graphite (HAPG). In some instances, the crystals may include HOPG(002) and HAPG(002). In some embodiments, a graphite layer between 15 and 200 microns thick is grown onto a curved substrate.

Dispersion is achieved because the diverging cone has a variety of angles of incidence on the crystal analyzer, and therefore for at least some angle of incidence, x-rays of a particular energy within the designated x-ray bandwidth may be reflected. However, all other wavelengths at the same angle of incidence will not be diffracted, and will simply pass through the crystal analyzer shown as transmitted x-rays 899 in FIGS. 11 and 12.

FIG. 12 illustrates a geometry of the spectrometer used in some embodiments. Spectrometer 3730 uses a crystal analyzer in the form of a mosaic crystal 3733. In the mosaic crystal 3733, the crystal analyzer comprises an ensemble of micro-crystals at varied angles throughout the material, each as small as a few hundred nanometers or as large as several microns, held with a backing 3734, typically made of metal. In some instances, the mosaic crystal can be curved at least in the sagittal non-dispersive direction. Transmitted x-rays that were not diffracted by the micro-crystal at the surface may still be diffracted from another micro-crystal positioned deeper within the mosaic.

The origin of x-rays (the focal point of the x-ray optics), the diffracting crystal, and the point of convergence at the detector all fall along the Rowland Circles 808-A and 808-D for the corresponding wavelengths. Although other microcrystals are present in the mosaic crystal, only those that lie along the Rowland Circle and have the correct orientation will diffract x-rays to converge to the same position at the detector 290. X-rays of varying wavelengths distributed throughout the diverging beam 888-T have a better chance of encountering a properly positioned and oriented micro-crystal. Use of mosaic crystals can collect as much as 100 times the amount of x-rays that a single crystal diffraction element can produce. Note that although micro-crystals with "random" orientations are illustrated to dramatically illustrate the mosaic non-uniformity, most mosaic crystals will be more aligned.

Figure 13A:
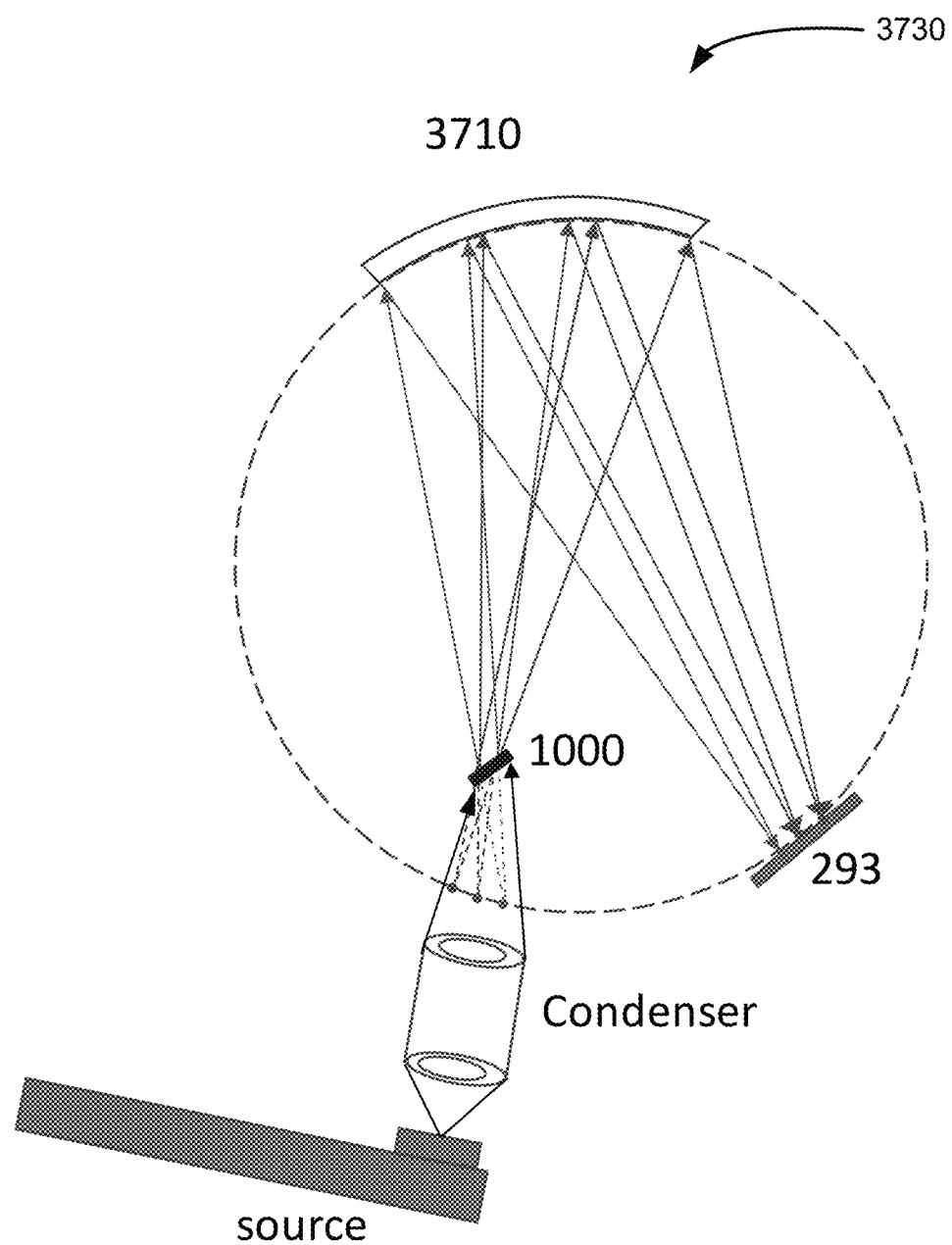
FIG. 13A-13D illustrate schematic views of disclosed spectrometers.

FIG. 13A illustrates a spectrometer design based on a Rowland Circle geometry with a crystal that is curved to Johansson geometry. In some instances, the crystal could be curved to Johann geometry. The crystals could be singly curved—that is, curved only in the dispersion plane and flat in the sagittal (or vertical) plane. In other instances, the crystals could be doubly curved—that is, curved in both dispersion and sagittal planes. Examples of such doubly curved crystals include, but not limited to, spherical Johann, Toroidal Johann, Spherical Johansson and Wittry crystals. As shown, an apparent source 272 behind the sample 1000 emits x-rays toward the Johansson crystal 3710. The apparent source is often produced by an apertured or focused x-ray beam generated from a laboratory x-ray source in combination with an optic as has been previously described, or in some instances, by electron bombardment of a sample in an electron microscope. In some instances, the focal spot of the focused x-ray beam is coincident with a sample—in other instances, the focal spot is behind the sample 1000 and is coincident with an aperture (not shown). The x-rays are transmitted through the sample and propagate towards Johansson crystal 3710, which focuses the x-rays to a spatially resolving detector 293. The placement of the apparent source 272 within the Rowland circle is known as an off-Rowland circle geometry.

Figure 13B:
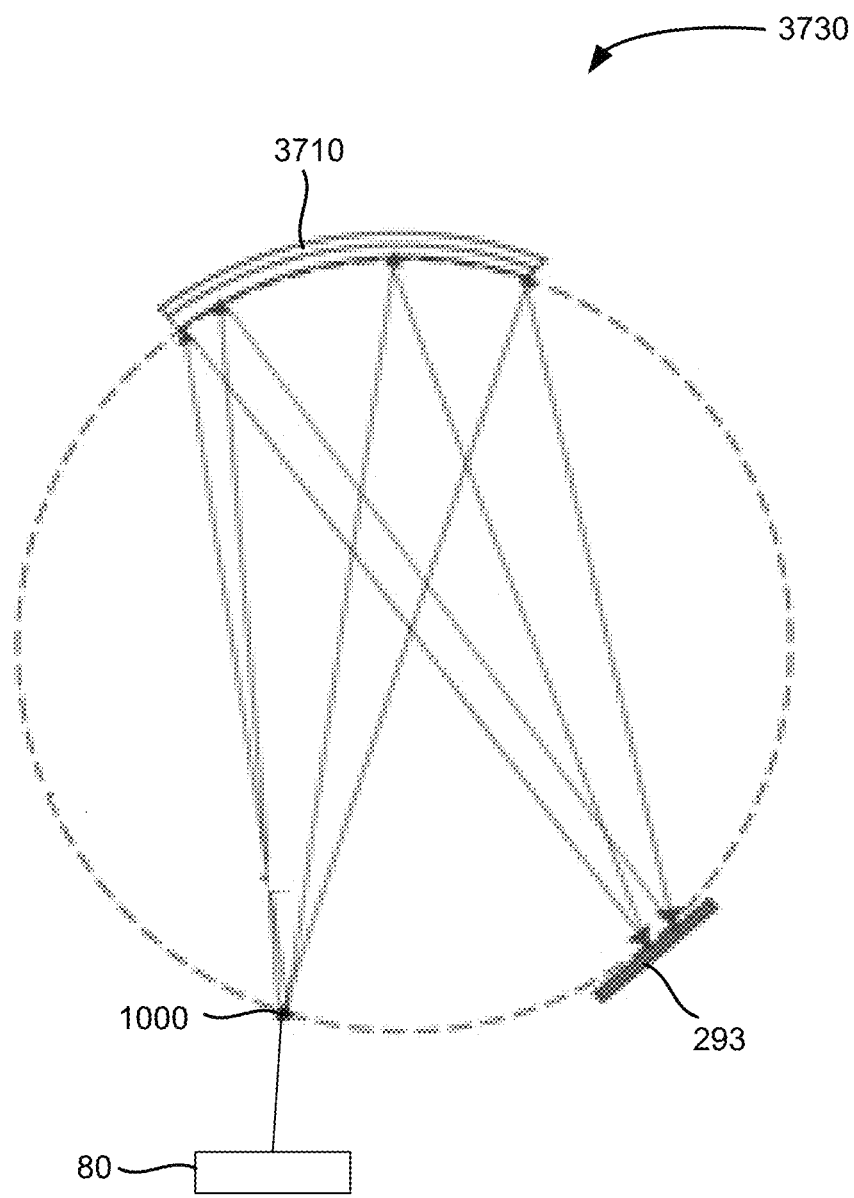

In some other implementations, as illustrated in FIG. 13B, a sample 1000 can be placed on the Rowland circle. The source 80 can be located further away from the Rowland circle and direct x-rays to the sample 1000, with an optional x-ray optic placed between the x-ray source 80 and the sample 1000. Note that the sample 1000 may furthermore be placed slightly before the focal point of a focusing optical system if it is employed. The sample acts as an apparent source of x-rays and crystal 3710 disperses the x-rays. The x-ray detector 293 simultaneously detects all the x-rays dispersed by the crystal 3710 over a certain angular range. The implementations illustrated in FIGS. 13A and 13B are sometimes referred to as parallel detection.

Figure 13C:
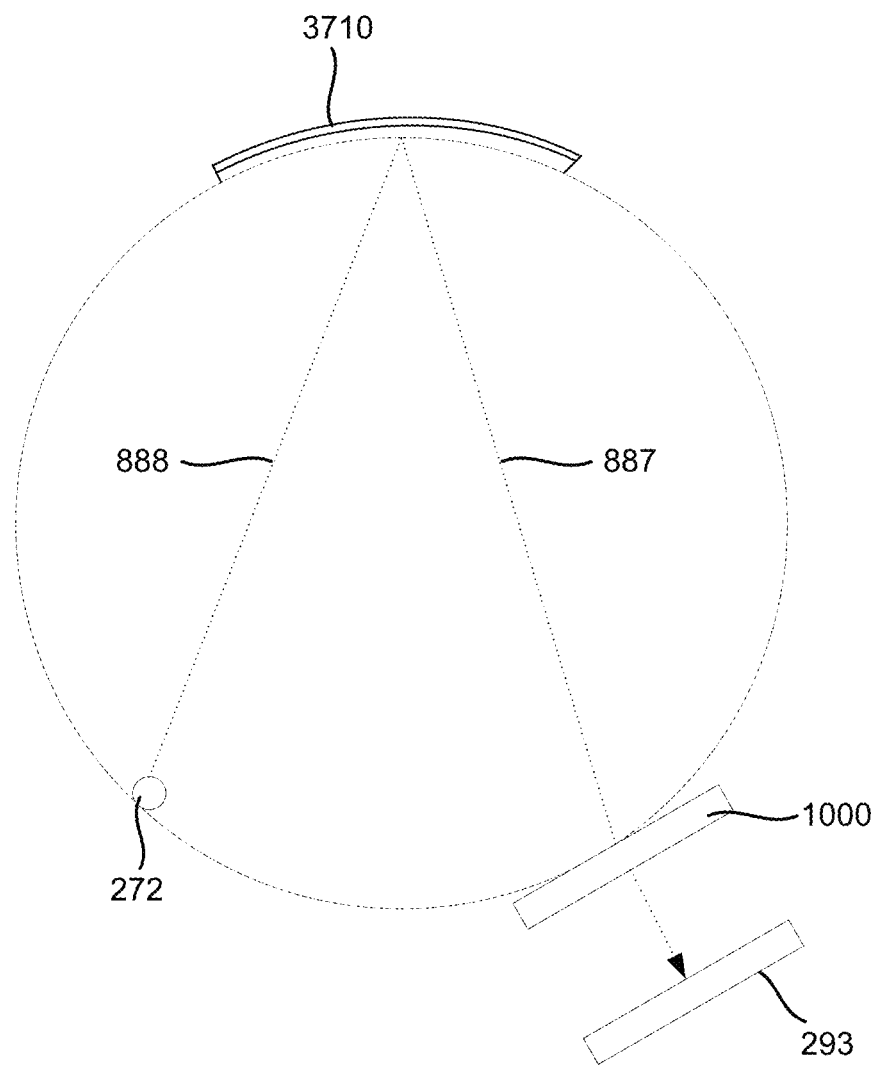

In some other implementations, as illustrated in FIG. 13C, sometimes referred to as serial detection or scanning geometry, an apparent source 272 is located on the Rowland circle and directs x-rays 888 to a Johann crystal 3710, which collects the x-rays and focuses x-rays 887 on the sample 1000 that is located on the Rowland circle. An x-ray detector 293 is behind the sample to collect all x-rays transmitted through the sample. The x-ray detector 293 could be a point detector such as, but not limited to, Silicon Drift Detector, Gaseous Proportional counter, solid state detectors etc. In such implementations, detection efficiency is optimized for only a single x-ray wavelength (or extremely narrow bandwidth of x-rays) rather than multiple wavelengths as in the case of parallel detection x-ray spectrometers. The relative alignment of the x-ray origin, crystal, and detector, as well as parameters of the Rowland Circle (e.g. diameter), can be changed by motion of one or more of the components.

In some embodiments in which x-ray absorption near edge spectroscopy (XANES) is more important to obtain than extended x-ray absorption fine structure (EXAFS), this is preferred. Note that XANES is considered pre-edge and edge information and EXAFS is above the absorption edge and although no clear principle definition distinguishes the two systems, general guidelines locate the XANES regime in the range where potential is within tens of eV (e.g. 50 eV) from the edge and EXAFS is where the potential begins anywhere from 20-50 eV above the edge and typically extends up to 1 keV over the edge.

In some embodiments, the sample may be a thin film or structure existing on a substrate that may be too thick for the x-rays of energies of interest to transmit through the sample. In such embodiments, reflection geometry may be preferred. The x-rays are typically incident on the sample at a very shallow incident angle, typically below a couple of degrees to meet the condition of total reflection at the film/substrate and/or structure/substrate interface. The x-rays penetrate through the film or structure of interest but get reflected at the interface of the film/substrate or structure/substrate interface and emerge from the same side of the sample as the incident beam. This avoids the problem of insufficient transmission of x-rays through the sample. Note that this geometry may be used for XANES and EXAFS.

5.2. Multi-Crystal Spectrometer

In some embodiments of the invention, the spectrometer may use different crystal types for different regimes of the x-ray absorption spectroscopy acquisition. In some embodiments, the spectrometer uses at least two different crystal types: with at least one being a single crystal and at least one being a mosaic crystal. In some embodiments, the single crystal may be a flat crystal that is aligned to measure the x-ray wavelength of interest. In preferred embodiments, the crystal is curved in a tangential direction (e.g. Johann, Johannsson).

The single crystal and an x-ray detector (typically referred to as a "single crystal spectrometer") are used for the acquisition of XANES information. An apparent source of x-rays, crystal, and detector are aligned such that the apparent source is either on or within a Rowland circle. The apparent sample spot is achieved by either an aperture or through direct focused illumination on the sample using an x-ray optical train. The Rowland circle is a circular geometry in which an apparent source of x-rays on the sample, the crystal, and a detector can be placed so that the spectral lines are to be brought into focus on the detector. In some embodiments, if the apparent source of x-rays is placed within the Rowland circle, multiple x-ray energies can be dispersed along the detector and an x-ray detector with energy dispersive capabilities can be used. In some embodiments, this may be a CCD detector with sufficiently fast readout speeds. In other embodiments, this may be an energy dispersive array detector. In some embodiments, if the apparent source of x-rays is placed on the Rowland circle, a narrow range of wavelengths is received by the detector.

In a subset of these implementations, the crystal may be used for serial detection by placing the single crystal on a Rowland circle. In other subsets of these implementations, the single crystal may be used for parallel detection by placing the apparent source of x-rays within a Rowland circle (off-Rowland geometry). Once The XANES spectrum is obtained, it can be then normalized by the direct beam spectrum acquired by removing the sample from the beam. Single crystals used may include Si(111), Si(220), Si(400), Ge(111), Ge(220), Ge(400), and Ge(620).

The mosaic crystal and at least one spatially resolving x-ray detector (referred to as a "mosaic crystal spectrometer") is used for the acquisition of EXAFS information. In some embodiments, the mosaic crystal is a curved in the sagittal direction and the apparent source, mosaic crystal, and detector are aligned in a parallel detector geometry. The system may then be used with a different set of crystals, such as HOPG crystals, to focus x-rays at a spatially resolving detector in a parallel detection geometry such as von Hamos for acquisition of EXAFS spectrum. The different set of crystals can be positioned in a position suitable for focusing x-rays at the spatially resolving detector. In some instances, the crystals may be interchangeable and positioned using electro-mechanical mechanisms, or may be stationary as a source is positioned to provide x-rays at the currently selected crystal. After the EXAFS spectrum is acquired, normalization can be performed by acquiring the direct beam spectrum by removing the sample from the beam.

The XANES and EXAFS data can be processed by a spectra processing mechanism, which can be implemented for example by signal processing electronics 292 an analysis system 295. Obtaining spectra in the energy range of 100 to 200 eV near and including the absorption edge energy, is common to both XANES and EXAFS spectra but the XANES spectrum is obtained at higher energy resolution. With appropriate overlay, normalization, correlation, stitching and processing using techniques well known in the several fields such as spectroscopy, imaging etc., the near edge portion of the EXAFS spectrum can be replaced with the XANES spectrum resulting in the XANES and EXAFS spectra combined together in a unique fashion to provide a complete XAS spectrum with no loss in information. Processing of the XANES spectra, for example by a single crystal spectrometer, and the EXAFS spectra, for example by a mosaic crystal spectrometer, produce x-ray absorption spectroscopy data in which the spectrum nearest to the absorption edge is refined with the higher spectral resolution spectrum. This unique method provides for a complete and a more refined XAS analysis.

In some embodiments, two spectrometer designs or a single spectrometer capable of being used in the above approach.

Figure 13D:
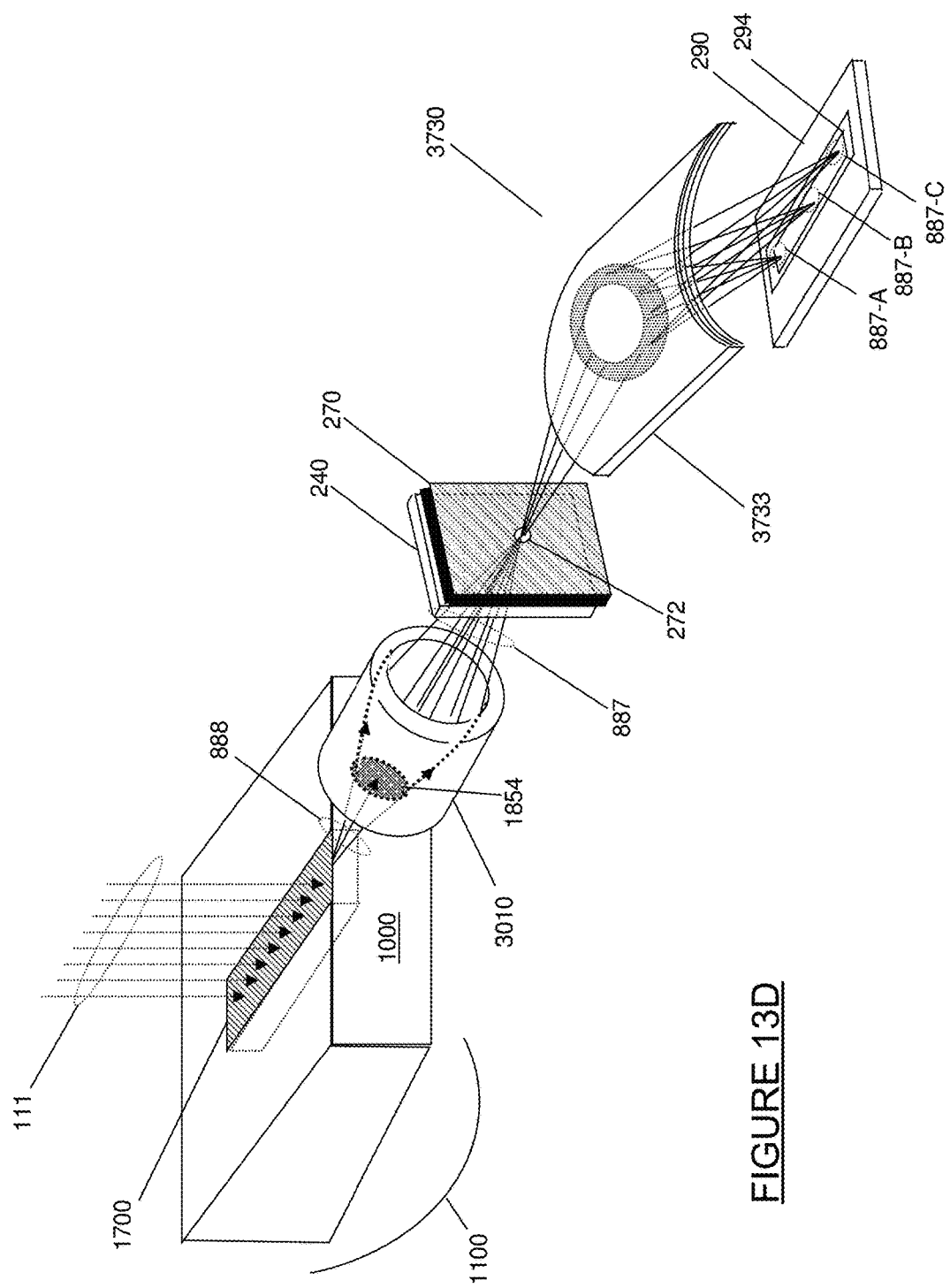

FIG. 13D illustrates a schematic perspective view of a system using a curved crystal analyzer that distributes the spectrum along one axis, while focusing x-rays in the other (sagittal) axis. As noted before, it should be clear that the drawings presented here are not illustrated to scale, but have been created to better point out how the invention is to be made and used.

For more on crystal or multilayer reflectors, see James H. Underwood, "Multilayers and Crystals", Section 4.1 of the X-ray Data Booklet, which may be downloaded at: xdb.lbl.gov/Section4/Sec_4-1.pdf.

5.3. Detectors.

In embodiments in which a wavelength dispersive geometry is used, the detector may be any x-ray counting detector.

In the embodiments in which a spatially resolving detector is used, the spatially resolving detector 290 may comprise a 2D or 1D array sensor 294. In some embodiments of 2D arrays, one axis may be significantly longer than the other. A 2048×256 pixel array may be used, although a detector with at least 128 pixels along the long axis (the dispersive direction) may be preferred. In such embodiments, it is preferred that the long axis will be aligned along the direction of x-ray propagation, and the dispersion of x-rays by wavelength will occur along that axis. The short axis will be aligned with the sagittal direction. In a perfect system with perfect sagittal focus, a 1-D array detector 1 pixel wide may be used, but as a practical matter, the diffracted x-rays may not form a perfect spot, and so detection using multiple pixels may provide a higher collection efficiency.

The spatially resolving detector 290 may be any one of a number of x-ray array detectors, such as a CCD array (x-ray sensor), a CMOS or S-CMOS detector, a flat panel sensor, or any one or more position sensitive x-ray array detectors known in the art that converts x-ray intensity to an electronic signal, including 1-D line and 2-D array detectors. Such examples of position-sensitive detectors include linear detectors, position-sensitive array detectors, pin diodes, proportional counters, spectrometers, photodiode detectors, scintillator-type and gas-filled array detectors, etc. In some embodiments, the detector may include one or more detector elements of any type that detects x-rays, including proportional and avalanche detectors or energy-dispersive elements.

Other detector variations may also be used in other embodiments of the invention. For example, additional spectral filters may be used between the object and the detector to select a certain portion of the x-rays emerging from the object for detection. This may be especially useful if there is a significant amount of x-ray fluorescence from the object that may interfere with the signals generated by the transmitted x-rays. Alternatively, a second detector may be included to detect the intensity of the incident x-rays, allowing normalization of the transmitted signal with any variations in the incident x-ray intensity.

Energy resolving pixel array detectors may also be used. In these detectors, each pixel also provides information on the energy of x-rays detected, and may be especially useful when the object produces significant fluorescence. The silicon PIN photodiode (Si-PIN) is a simple and low cost class of EDS spectrometer that typically has the lowest performance in terms of energy resolution. Energy resolving pixel array spectrometers are available and may be used in some embodiments of the invention. Another type of detector is known as a pixel array microcalorimeter spectrometer. In some instances, a CCD detector with a sufficiently fast readout speed serves as an energy resolving detector.

Additional configurations may involve additional filters (e.g. thin foils containing the appropriate element(s)) along the beam path before the detector to preferentially attenuate some unwanted x-rays from arriving at the spectrometer, reducing the background due to the detection of the x-rays scattered from the object or reduce total x-ray flux entering by the spectrometer to avoid saturation. Multiple spectrometers of the same type or combination of two or more types can be used simultaneously or interchangeable to utilize their respective strength individually or collectively.

In some embodiments, an aperture or slit component may be placed before the detector. Other detector geometries and arrangements for x-ray fluorescence may be known to those skilled in the art. For more on x-ray detectors, see Albert C. Thompson, "X-Ray Detectors", Section 4.5 of the X-ray Data Booklet, which may be downloaded at: xdb.lbl.gov/Section4/Sec_4-5.pdf.

5.4. Options and Versatility.

Figure 14:
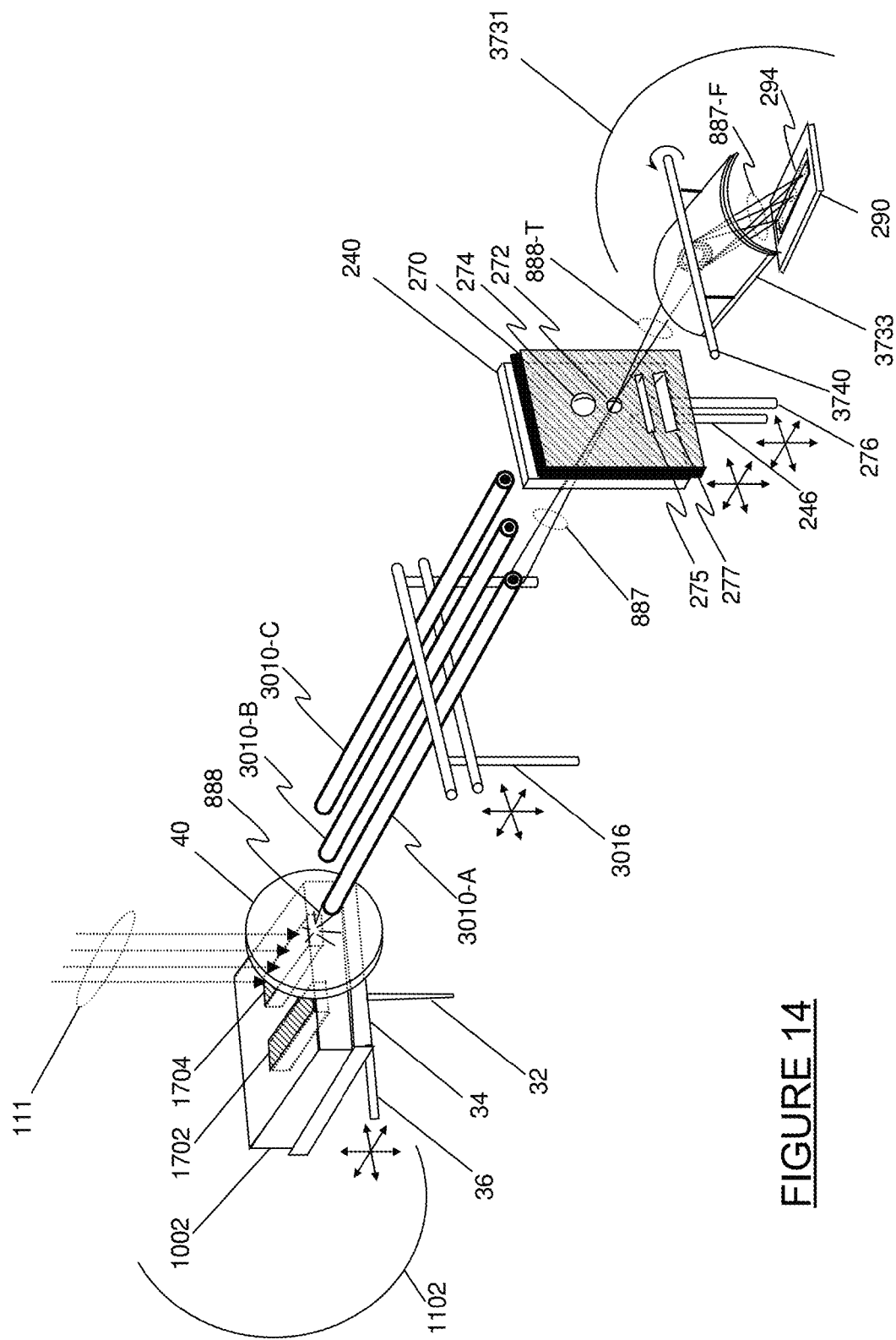
FIG. 14 illustrates a perspective schematic view of a spectrometer system having multiple options for x-ray source, optical train, aperture, and analyzer crystal position.

FIG. 14 provides a schematic illustration of a spectrometer system having a diversity of options built into the system.

The target 1102 comprises a substrate 1002 and two (or more) different types of x-ray generating materials 1702 and 1704. The mount 34 upon which the target is secured not only connects to the electrical lead 32, but also has a controller 36 that allows physical motion in a lateral direction for the selection of the material to be bombarded by electrons 111.

The system of FIG. 14 also has multiple different optical trains 3010-A, 3010-B and 3010-C supported in a mount 3016 that allows the set of optical trains to be moved laterally to allow alignment of any of the optical trains (which may use different material coatings and filters inside to allow different x-ray bandwidths) with any of the x-ray generating targets 1702, 1704 etc. As illustrated, the rightmost x-ray generating material 1704 is being bombarded by electrons, and the left most optical train 3010-A is positioned to collect the x-rays transmitted through the window 40. The mount that provides for movement of the x-ray optical systems allows for selecting which x-ray optical system will collect x-rays from the x-ray source.

As before, the converging x-rays 887 emerging from the optical train are focused onto an aperture 272 in an aperture component 270, and also pass through the object 240 to be investigated. The resulting x-rays diverging from the aperture 272 become the apparent source of the x-rays diffracted by the spectrometer 3700.

However, the aperture component 270 may have multiple openings, such as circular apertures 272 and 274 having different sizes, or slits 275 and 277 of different sizes.

As before, the spectrometer 3731 comprises a mosaic analyzer crystal 3733 that disperses the x-rays onto the x-ray sensor 294 of the detector 290. However, in case the wavelength range is insufficient to span the entire spectrum in a single shot, this spectrometer 3731 also comprises a mount 3740 that allows the analyzer crystal 3710 to rotate about an axis perpendicular to the direction of x-ray propagation. This allows a larger range of x-ray dispersion to be measured using a single detector.

Such a multi-source/multi optic system may be used to collect x-ray spectra in a sequence of bands (e.g. combinations for different 1 keV bands). Rotation of the crystal about the axis may expand the range of energies collected by from the same source/optic combination.

In other variations, optical trains with a variety of beam stops may be used. Beam stops may be positioned at the entrance to the optical train, at the exit of the optical elements of the optical train, or in between elements of the optical train. In some embodiments with a single condenser optic, there may be a stop on both the entrance side and the exit side of the condenser optic, with the exit-side stop being ~⅔ the size of entrance stop. These stops will both block the through-beam, and in addition, the exit stop will also block a good portion of any scattered x-rays from the condenser optic. This provides for a cleanly reflected x-ray beam.

In other variations, a number of shielding elements may be used to block or reduce unwanted x-rays from being detected. In some variations, an x-ray fluorescence detector is used to monitor incident x-rays and/or monitor the elemental composition of the sample. In other variations, the entire system (and not just the x-ray source) may be enclosed in a vacuum chamber, removing the need for the window 40 be present to maintain the vacuum around the x-ray source. Likewise, the optical train and spectrometer may be flushed with helium gas, to reduce scattering in the system.

In some variations, the sample is moved relative to the spectrometer to perform 2D mapping or 3D tomography of XAS information.

5.4. Method

Figure 15:
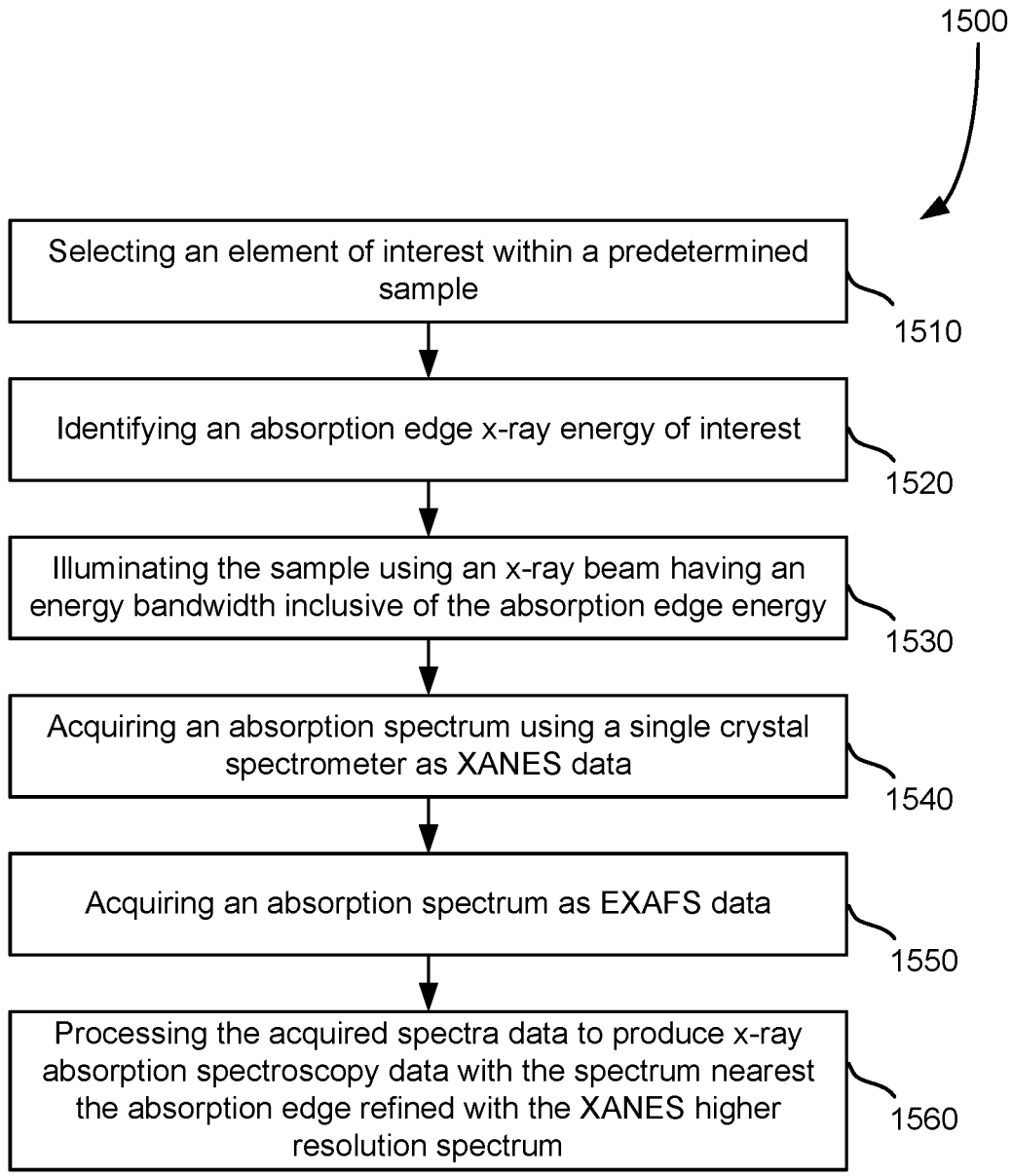
FIG. 15 illustrates a flowchart of a method for obtaining x-ray absorption spectroscopy information.

FIG. 15 illustrates a method for efficiently obtaining x-ray absorption spectroscopy information using multiple crystals. An element of interest is selected within a predetermined sample at step 1510. In some instances, the element may be selected by an x-ray absorption spectrometer (XAS) system in response to receiving input from a user. An absorption edge x-ray energy of interest may then be identified at step 1520. In some instances, the absorption edge can be identified by the present system in response to user input received by the present system.

The sample can be illuminated using an x-ray beam having an x-ray bandwidth inclusive of the absorption edge energy at step 1530. The x-ray beam can be provided by micro-focus x-ray source or other source. The absorption edge may be for an element of interest within the predetermined sample.

A first absorption spectrum is acquired using a single crystal spectrometer as XANES data at step 1540. The absorption spectrum can be acquired at high spectral resolution of greater than, for example, 3 eV, for a bandwidth of x-ray energies near and inclusive of the selected absorption edge.

A second absorption spectrum is acquired using a mosaic crystal spectrometer as EXAFS data at step 1550. The EXAFS data can have a coarser spectral resolution than the XANES data absorption spectrum acquired using the single crystal spectrometer. The second spectrum is acquired for a bandwidth of x-ray energies wider than the bandwidth of x-rays acquired by the single crystal spectrometer. The absorption spectrum can be inclusive of the absorption edge such that the absorption spectrum data acquired using the mosaic crystal spectrometer contains at least the extended x-ray absorption fine structure (EXAFS) data.

The acquired XANES spectra data and EXAFS spectra data can be processed to produce x-ray absorption spectroscopy data at step 1560. The produced x-ray absorption spectroscopy data nearest to the absorption edge is refined with the higher spectral resolution spectrum obtained by the single crystal spectrometer.

In some embodiments, only one absorption spectrum will be acquired by either a single crystal spectrometer as XANES or a mosaic crystal spectrometer as EXAFS. The results will be compared to a library of standards as a "fingerprint" for refining the analysis.

6. Limitations and Extensions.

With this Application, several embodiments of the invention, including the best mode contemplated by the inventors, have been disclosed. It will be recognized that, while specific embodiments may be presented, elements discussed in detail only for some embodiments may also be applied to others. Also, details and various elements described as being in the prior art may also be applied to various embodiments of the invention.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

What is claimed is:

1. A method for performing x-ray absorption spectroscopy, the method comprising:
    illuminating an object using an x-ray beam with an energy bandwidth greater than 0.1% and inclusive of the energy corresponding to an absorption edge of an atomic element;
    acquiring a first x-ray absorption spectrum from the object at a first energy resolution better than 3 eV, using a single crystal spectrometer, over a first energy bandwidth inclusive of the absorption edge;
    acquiring a second x-ray absorption spectrum from the object using a mosaic crystal spectrometer at a second energy resolution coarser than the first energy resolution and over a second energy bandwidth wider than the first energy bandwidth; and
    processing the first and second x-ray absorption spectra to produce a third x-ray absorption spectrum in which the second x-ray absorption spectrum within the first energy bandwidth corresponding to the first x-ray absorption spectrum is refined using the first x-ray absorption spectrum.

2. The method of claim 1, further comprising focusing the x-ray beam on the object using at least one capillary reflective x-ray focusing optic, the energy bandwidth of the x-ray beam inclusive of the absorption edge and having energies greater than 100 eV above the absorption edge.

3. The method of claim 1, wherein the single crystal spectrometer comprises a single crystal curved at least in the dispersion plane.

4. The method of claim 3, wherein acquiring the first x-ray absorption spectrum comprises using a spatially resolving detector to detect x-rays dispersed by single crystal while the sample, the single crystal, and the spatially resolving detector are in an off-Rowland circle geometry.

5. The method of claim 1, wherein the first x-ray absorption spectrum contains at least part of an x-ray absorption near edge structure (XANES) spectrum.

6. The method of claim 1, wherein the mosaic crystal spectrometer comprises a mosaic crystal curved at least in the sagittal direction of dispersion, and acquiring the second x-ray absorption spectrum comprises using a spatially resolving x-ray detector to detect x-rays dispersed by the mosaic crystal while the mosaic crystal and the spatially resolving detector are in an Von Hamos geometry.

7. A system for performing x-ray absorption spectroscopy, the system comprising:
an x-ray source;
a mount configured to support an object to be examined;
at least one focusing x-ray optic configured to collect x-rays from said x-ray source with an energy bandwidth greater than 0.1% of an x-ray energy corresponding to an absorption edge of an atomic element to be detected in the object, the energy bandwidth inclusive of the x-ray energy corresponding to the absorption edge, the at least one focusing x-ray optic further configured to focus a portion of the collected x-rays onto a focal spot at the object with a focus size less than 500 micrometers;
at least one single crystal spectrometer with an energy resolution better than 3 eV, the at least one single crystal spectrometer comprising:
at least one single crystal analyzer curved at least in the dispersion direction, and
at least one spatially resolving x-ray detector configured to detect x-rays transmitted through the object;
and in which the focal spot, said at least one single crystal analyzer, and said at least one spatially resolving x-ray detector are positioned in an off-Rowland circle geometry.

8. The system of claim 7, wherein the at least one focusing x-ray optic comprises a capillary x-ray optic having an interior reflecting surface, wherein at least a portion of the interior reflecting surface is a portion of a quadric surface.

9. The system of claim 7, wherein a reflecting surface of the at least one focusing x-ray optic comprises multilayer coatings.

10. The system of claim 7, wherein the x-ray source comprises a plurality of x-ray target materials and an electron beam generator configured to generate an electron beam and to bombard a selected x-ray target material of the plurality of x-ray target materials with the electron beam.

11. A system for performing x-ray absorption spectroscopy, the system comprising:
an x-ray source;
a mount configured to support an object to be examined;
at least one focusing x-ray optic configured to collect x-rays from the x-ray source and to focus at least a portion of the collected x-rays onto a focal spot at the object with a focus size less than 500 micrometers;
at least one spatially resolving x-ray detector;
at least one single crystal curved at least in the dispersion direction, the focal spot, the at least one single crystal, and the at least one spatially resolving x-ray detector configured to be in an off-Rowland circle geometry;
at least one mosaic crystal curved at least in the sagittal direction, the focal spot, the at least one mosaic crystal, and the at least one spatially resolving x-ray detector configured to be in a Von Hamos geometry; and
a processing system configured to normalize and align a single-crystal x-ray absorption spectrum obtained with the single crystal and a mosaic-crystal x-ray absorption spectrum obtained with the mosaic crystal to produce a combined x-ray absorption spectrum in which the mosaic-crystal x-ray absorption spectrum within an energy bandwidth corresponding to the single-crystal x-ray absorption spectrum is refined using the single-crystal x-ray absorption spectrum.

12. The system of claim 11, wherein the single-crystal x-ray absorption spectrum has an energy resolution better than 3 eV over an energy bandwidth of 10 eV to 100 eV.

13. The system of claim 11, wherein the mosaic-crystal x-ray absorption spectrum has an energy resolution coarser than 3 eV over an energy bandwidth over 100 eV.

14. The system of claim 11, wherein the said at least one focusing x-ray optic is configured to collect the x-rays from the x-ray source with an energy bandwidth greater than 0.1% of an absorption edge of a predetermined atomic element and inclusive of the absorption edge of the predetermined atomic element.

15. The system of claim 14, wherein the at least one focusing x-ray optic comprises a capillary x-ray optic having an interior reflecting surface, wherein at least a portion of the interior reflecting surface is a portion of a quadric surface.

16. The system of claim 15, wherein the portion of the interior reflecting surface is coated with a material with atomic number greater than 26 and is axially symmetric.

17. The system of claim 14, furthermore comprising an aperture configured to selectively pass x-rays transmitted through the object while not passing fluorescence x-rays from the object.

18. The system of claim 11, wherein the x-ray source comprises a plurality of x-ray target materials and an electron beam generator configured to generate an electron beam and to bombard a selected x-ray target material of the plurality of x-ray target materials with the electron beam.

19. The system of claim 11, wherein the focal spot, the single crystal, and the at least one spatially resolving x-ray detector are configured to change a distance between the focal spot and the single crystal to select the energy bandwidth of the single-crystal x-ray absorption spectrum.

20. The method of claim 5, wherein the second x-ray absorption spectrum contains at least extended x-ray absorption fine structure (EXAFS) data.

* * * * *